US010034705B2

(12) United States Patent
Buysman et al.

(10) Patent No.: US 10,034,705 B2
(45) Date of Patent: Jul. 31, 2018

(54) HIGH STRENGTH ELECTRODE ASSEMBLY FOR CATHETER SYSTEM INCLUDING NOVEL ELECTRODE

(71) Applicant: St. Jude Medical, Cardiology Division, Inc., St. Paul, MN (US)

(72) Inventors: John Jason Buysman, Minnetonka, MN (US); Ryan Kenneth Buesseler, Delano, MN (US); Qingshan Ye, Plymouth, MN (US); Victor Yevgenyevich Kotov, Minnetonka, MN (US); Gregory James Dakin, Edina, MN (US); Russ Terwey, St. Michael, MN (US); Janson Lee Ayer, Maple Grove, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 813 days.

(21) Appl. No.: 14/521,865

(22) Filed: Oct. 23, 2014

(65) Prior Publication Data
US 2015/0119883 A1    Apr. 30, 2015

Related U.S. Application Data

(60) Provisional application No. 61/895,183, filed on Oct. 24, 2013.

(51) Int. Cl.
*A61B 18/18* (2006.01)
*A61B 18/14* (2006.01)
*A61B 18/00* (2006.01)

(52) U.S. Cl.
CPC ............. *A61B 18/1492* (2013.01); *A61B 2018/00267* (2013.01); *A61B 2018/00577* (2013.01); *A61B 2018/00952* (2013.01)

(58) Field of Classification Search
USPC ........................................................ 606/41
See application file for complete search history.

(56) References Cited

U.S. PATENT DOCUMENTS 3,650,277 A    3/1972   Sjostrand et al.
4,658,819 A    4/1987   Harris et al.
(Continued)

FOREIGN PATENT DOCUMENTS

WO    97/45157    12/1997
WO    00/66020    11/2000
(Continued)

OTHER PUBLICATIONS

Robbins, Ivan M. et al, Pulmonary Vein Stenosis After Catheter Ablation of Atrial Fibrillation, Circulation Journal of The American Heart Association, 1998;98:1769-1775.
(Continued)

*Primary Examiner* — Nicole F Johnson
(74) *Attorney, Agent, or Firm* — Armstrong Teasdale LLP (57) ABSTRACT

The present disclosure is directed to electrode assemblies, and specifically to struts comprising electrode assemblies and electrodes contained on the struts. The electrode assembly struts are constructed to have a low profile and to have superior strength over the length of the strut such that an electrode assembly including the strut is highly resistant to radial compression. The electrodes included on the low profile, high strength strut also is designed to have a reduced profile such that electrode assemblies including the strut and electrode can easily be used with 6 French and smaller guide catheter assemblies.

9 Claims, 5 Drawing Sheets

(56) References Cited

U.S. PATENT DOCUMENTS

| | | | |
|---|---|---|---|
| 5,035,694 A | 7/1991 | Kasprzyk et al. |
| 5,255,679 A | 10/1993 | Imran |
| 5,300,068 A | 4/1994 | Rosar et al. |
| 5,368,591 A | 11/1994 | Lennox et al. |
| 5,387,233 A | 2/1995 | Alferness et al. |
| 5,465,717 A | 11/1995 | Imran et al. |
| 5,531,779 A | 7/1996 | Dahl et al. |
| 5,598,848 A | 2/1997 | Swanson et al. |
| 5,607,462 A | 3/1997 | Imran |
| 5,628,313 A | 5/1997 | Webster, Jr. |
| 5,676,662 A | 10/1997 | Fleischhacker et al. |
| 5,707,400 A | 1/1998 | Terry, Jr. et al. |
| 5,769,077 A | 6/1998 | Lindegren |
| 5,772,590 A | 6/1998 | Webster, Jr. |
| 5,893,885 A | 4/1999 | Webster, Jr. |
| 5,897,553 A | 4/1999 | Mulier et al. |
| 5,954,649 A | 9/1999 | Chia et al. |
| 5,954,719 A | 9/1999 | Chen et al. |
| 6,004,269 A | 12/1999 | Crowley et al. |
| 6,012,457 A | 1/2000 | Lesh |
| 6,016,437 A | 1/2000 | Tu et al. |
| 6,024,740 A | 2/2000 | Lesh et al. |
| 6,073,048 A | 6/2000 | Kieval et al. |
| 6,096,037 A | 8/2000 | Mulier et al. |
| 6,117,101 A | 9/2000 | Diederich et al. |
| 6,161,543 A | 12/2000 | Cox et al. |
| 6,178,349 B1 | 1/2001 | Kieval |
| 6,200,312 B1 | 3/2001 | Zikorus et al. |
| 6,216,044 B1 | 4/2001 | Kordis |
| 6,233,491 B1 | 5/2001 | Kordis et al. |
| 6,283,951 B1 | 9/2001 | Flaherty et al. |
| 6,287,608 B1 | 9/2001 | Levin et al. |
| 6,292,695 B1 | 9/2001 | Webster, Jr. et al. |
| 6,322,559 B1 | 11/2001 | Daulton et al. |
| 6,460,545 B2 | 10/2002 | Kordis |
| 6,522,926 B1 | 2/2003 | Kieval et al. |
| 6,613,045 B1 | 9/2003 | Laufer et al. |
| 6,616,624 B1 | 9/2003 | Kieval |
| 6,635,054 B2 | 10/2003 | Fjield et al. |
| 6,656,174 B1 | 12/2003 | Hedge et al. |
| 6,669,655 B1 | 12/2003 | Acker et al. |
| 6,699,231 B1 | 3/2004 | Sterman et al. |
| 6,748,255 B2 | 6/2004 | Fuimaono et al. |
| 6,805,131 B2 | 10/2004 | Kordis |
| 6,845,267 B2 | 1/2005 | Harrison et al. |
| 6,954,977 B2 | 10/2005 | Maguire et al. |
| 6,970,730 B2 | 11/2005 | Fuimaono et al. |
| 7,122,031 B2 | 10/2006 | Edwards et al. |
| 7,149,574 B2 | 12/2006 | Yun et al. |
| 7,155,284 B1 | 12/2006 | Whitehurst et al. |
| 7,162,303 B2 | 1/2007 | Levin et al. |
| 7,245,955 B2 | 7/2007 | Rashidi |
| 7,291,146 B2 | 11/2007 | Steinke et al. |
| 7,363,076 B2 | 4/2008 | Yun et al. |
| 7,419,486 B2 | 9/2008 | Kampa |
| 7,465,288 B2 | 12/2008 | Dudney et al. |
| 7,468,062 B2 | 12/2008 | Oral et al. |
| 7,481,803 B2 | 1/2009 | Kesten et al. |
| 7,653,438 B2 | 1/2010 | Deem et al. |
| 7,717,948 B2 | 5/2010 | Demarais et al. |
| 7,742,795 B2 | 6/2010 | Stone et al. |
| 7,850,685 B2 | 12/2010 | Kunis et al. |
| 7,949,407 B2 | 5/2011 | Kaplan et al. |
| 8,145,316 B2 | 3/2012 | Deem et al. |
| 8,224,416 B2 | 7/2012 | de la Rama et al. |
| 8,343,213 B2 | 1/2013 | Salahieh et al. |
| 8,347,891 B2 | 1/2013 | Demarais et al. |
| 8,442,639 B2 | 5/2013 | Walker et al. |
| 8,454,594 B2 | 6/2013 | Demarais et al. |
| 8,545,495 B2 | 10/2013 | Scheib |
| 9,022,948 B2 | 5/2015 | Wang |
| 2002/0068885 A1 | 6/2002 | Harhen et al. |
| 2002/0120304 A1 | 8/2002 | Mest |
| 2003/0050681 A1 | 3/2003 | Pianca et al. |
| 2003/0060858 A1 | 3/2003 | Kieval et al. |
| 2003/0074039 A1 | 4/2003 | Puskas |
| 2003/0114739 A1 | 6/2003 | Fuimaono et al. |
| 2003/0216792 A1 | 11/2003 | Levin et al. |
| 2003/0233099 A1 | 12/2003 | Danaek et al. |
| 2004/0215186 A1 | 10/2004 | Cornelius et al. |
| 2005/0221671 A1* | 10/2005 | Lyu ............... H01R 13/5224 439/587 |
| 2005/0288730 A1 | 12/2005 | Deem et al. |
| 2006/0089678 A1 | 4/2006 | Shalev |
| 2007/0135875 A1 | 6/2007 | Demarais et al. |
| 2008/0255478 A1 | 10/2008 | Burdette |
| 2009/0076409 A1 | 3/2009 | Wu et al. |
| 2010/0016762 A1 | 1/2010 | Thapliyal et al. |
| 2010/0063478 A1* | 3/2010 | Selkee ............... A61B 5/042 604/524 |
| 2010/0094209 A1 | 4/2010 | Drasler et al. |
| 2010/0168737 A1 | 7/2010 | Grunewald |
| 2010/0249773 A1 | 9/2010 | Clark et al. |
| 2010/0268307 A1 | 10/2010 | Demarais et al. |
| 2010/0286684 A1 | 11/2010 | Hata et al. |
| 2011/0004087 A1 | 1/2011 | Fish et al. |
| 2011/0118726 A1 | 5/2011 | de la Rama et al. |
| 2011/0137298 A1 | 6/2011 | Nguyen et al. |
| 2011/0160720 A1 | 6/2011 | Johnson |
| 2011/0213231 A1 | 9/2011 | Hall et al. |
| 2011/0257641 A1 | 10/2011 | Hastings et al. |
| 2011/0264011 A1 | 10/2011 | Wu et al. |
| 2011/0264086 A1 | 10/2011 | Ingle |
| 2012/0143097 A1 | 6/2012 | Pike, Jr. |
| 2012/0143298 A1 | 6/2012 | Just et al. |
| 2012/0157993 A1* | 6/2012 | Jenson ............... A61B 18/1492 606/41 |
| 2012/0296232 A1 | 11/2012 | Ng |
| 2012/0323233 A1 | 12/2012 | Maguire et al. |
| 2013/0116737 A1 | 5/2013 | Edwards et al. |
| 2013/0131743 A1 | 5/2013 | Yamasaki et al. |
| 2013/0144251 A1 | 6/2013 | Sobotka |
| 2013/0172715 A1 | 7/2013 | Just et al. |

FOREIGN PATENT DOCUMENTS

| | | |
|---|---|---|
| WO | 01/00273 | 1/2001 |
| WO | 01/22897 | 4/2001 |
| WO | 02/26314 | 4/2002 |
| WO | 03/082080 | 10/2003 |
| WO | 20061041881 | 4/2006 |
| WO | 2007/149970 | 12/2007 |
| WO | 2008/141150 | 11/2008 |
| WO | 2008/151001 | 12/2008 |
| WO | 2012/064818 | 5/2012 |
| WO | 2012/106492 | 8/2012 |

OTHER PUBLICATIONS

Rocha-Singh, Krishna J., Catheter-Based Sympathetic Renal Denervation A Novel Strategy for the Treatment of Resistant Hypertension, Endovascular Today, Aug. 2009, 52-56.

Rocha-Singh, Krishna J., Renal Artery Denervation: A Brave New Frontier, Endovascular Today, Feb. 2012, 45-53.

Sanderson, John E. et al, Effect of B-Blockade on Baroreceptor and Autonomic Function in Heart Failure, Clinical Science (1999) 96, 137-146.

Santos, Mario et al, Renal Sympathetic Denervation in Resistant Hypertension, World J Cardiol Apr. 26, 2013; 5(4):94-101.

Savard, Sebastien et al, Eligibility for Renal Denervation in Patients With Resistant Hypertension When Enthusiasm Meets Reality in Real-Life Patients, J Am Coll Cardiol. 2012;60(23):2422-2424.

Schauerte, Patrick et al, Catheter Ablation of Cardiac Autonomic Nerves for Prevention of Vagal Atrial Fibrillation, Circulation Journal of The American Heart Association, 2000, 102:2774-2780.

Schlaich, Markus P. et al, International Expert Consensus Statement: Percutaneous Transluminal Renal Denervation for the Treatment of Resistant Hypertension, Journal of the American College of Cardiology vol. 62, Issue 22, Dec. 3, 2013, pp. 2031-2045.

Schlaich, Markus P. et al, Renal Denervation as a Therapeutic Approach for Hypertension Novel Implications for an Old Concept,

(56) References Cited

OTHER PUBLICATIONS

Hypertension Journal of The American Heart Association, 2009;54:1195-1201.

Schlaich, Markus P. et al, Renal Sympathetic-Nerve Ablation for Uncontrolled Hypertension, The New England Journal of Medicine, 2009; 361:932-934.

Schmieder, Roland E. et al, ESH Position Paper: Renal Denervation—An Iterventional Therapy of Resistant Hypertension, Journal of Hypertension, 2012, 30:837-841.

Schmieder, Roland E. et al, Updated EHS Position Paper on Interventional Therapy of Resistant Hypertension, EuroIntervention 2013; 9:R58-R66.

Sellers, Alfred M. et al, Adrenalectomy and Sympathectomy for Hypertension Ten Year Survival, Archives of Surgery, vol. 89, Nov. 1964, 880-886.

Sen, S.K., Some Observations on Decapsulation and Denervation of the Kidney, The British Journal of Urology, vol. 8, Issue 4, Dec. 1936, 319-328.

Shiraki, Iwao William, Correction of Renal Hypertension by Ligation of Stenotic Segmental Renal Artery, Urology, vol. IX, No. 3, Mar. 1977, 296-298.

Shonai, Takaharu et al, Renal Artery Aneurysm: Evaluation with Color Doppler Ultrasonography Before and After Percutaneous Transarterial Embolization, J Ultrasound Med 19:277-280, 2000.

Silver, Donald et al, Renovascular Hypertension From Renal Artery Compression by Congenital Bands, Annals of Surgery, Feb. 1976, 161-166.

Smith, Gardner W. et al, Surgical Results and the Diagnostic Evaluation of Renovascular Hypertension, Annals of Surgery, May 1968, 669-680.

Smith, Harold P. et al, Radiofrequency Neurolysis in a Clinical Model Neuropathological Correlation, J Neurosurg 55:246-253, 1981.

Smithwick, R.H., An Evaluation of the Surgical Treatment of Hypertension, The Bulletin, Nov. 1949; 25(11):698-716.

Smithwick, Reginald H. et al, Splanchnicectomy for Essential Hypertension, The Journal of The American Medical Association, vol. 152, No. 16, Aug. 1953, 1501-1504.

Solis-Herruzo, J.A. et al, Effects of Lumbar Sympathetic Block on Kidney Function in Cirrhotic Patients with Hepatorenal Syndrome, Journal of Hepatology, 1987; 5: 167-173.

Sowers, James R. et al, Diabetes, Hypertension, and Cardiovascular Disease: An Update, Hypertension Journal of The American Heart Association, 2001;37:1053-1059.

Stanley, James C., Surgical Treatment of Renovascular Hypertension, The American Journal of Surgery, vol. 174, Aug. 1997, 102-110.

Stella, Andrea et al, Effects of Reversible Renal Denervation on Haemodynamic and Excretory Functions of the Ipsilateral and Contralateral Kidney in the Cat, Journal of Hypertension 1986, 4: 181-188.

Stuart, Candace, Newest Frontier in Cardiac Care: Kidneys; Cardiovascular Business, Dec. 13, 2012.

Stuart, Mary, Masterminds of Ardian: An Interview With Inventors Mark Gelfand and Howard Levin, Windhover Information, Start-Up Jan. 1, 2011.

Sun, Yingxian et al, Risk of Coronary Stenosis with Venous Ablation for Epicardial Accessory Pathways, PACE, Apr. 2001, Part II, vol. 24, 605.

Swartz, John F. et al, Radiofrequency Endocardial Catheter Ablation of Accessory Atrioventricular Pathway Atrial Insertion Sites, Circulation Journal of The American Heart Association, 1993;87:487-499.

Teigen, Corey L. et al, Segmental Renal Artery Embolization for Treatment of Pediatric Renovascular Hypertension, Journal of Vascular and Interventional Radiology, 1992; 3:111-117.

Teixeira, Maria Do Carmo et al,1992; Role of the Peripheral Renin Profile in Predicting Blood Pressure Control After Bilateral Nephrectomy in Renal-Transplanted Patients, Nephrol Dial Transplant (1998) 13: 2092-2097.

Teo, W S et al, Radiofrequency Catheter Ablation of Accessory Pathways: The Initial Experience in Singapore, Singapore Medical Journal, 1994; vol. 35:36-40.

Thiebot, J. et al, Bilateral Nephrectomy by Embolization of the Renal Arteries: A Report on Five Cases (author's transl), Sem Hop. Apr. 8-15, 1980;56(13-14):670-5.

Thomas, George et al, Renal Denervation to Treat Resistant Hypertension: Guarded Optimism, Cleveland Clinic Journal of Medicine, vol. 79, No. 7, Jul. 2012, 501-510.

Thomas, Natalie A., Secondary Consideration in Nonobviousness Analysis: The Use of Objective Indicia Following KSR v. Teleflex, NYU Law Review, vol. 86, No. 6, Dec. 2011, 2070-2112.

Ting, Chih-Tai et al, Arterial Hemodynamics in Human Hypertension Effects of Angiotensin Converting Enzyme Inhibition, Hypertension Journal of The American Heart Association, 1993;22:839-846.

Uchida, Fumiya et al, Effect of Radiofrequency Catheter Ablation on Parasympathetic Denervation: A Comparison of Three Different Ablation Sites, PACE, vol. 21, Nov. 1998, Part II, 2517-2521.

Valente, John F. et al, Laparoscopic Renal Denervation for Intractable ADPKD-Related Pain, Nephrol Dial Transplant (2001) 16:160.

Villarreal, Daniel et al, Effects of Renal Denervation on Postprandial Sodium Excretion in Experimental Heart Failure, American Journal of Physiology, May 1994;266(5 Pt 2):R1599-R1604.

Vonend, Oliver et al, Secondary Rise in Blood Pressure After Renal Denervation, The Lancet, vol. 380, Issue 9843, p. 778, Aug. 25, 2012.

Vujaskovic, Z. et al, Effects of Intraoperative Hyperthermia on Canine Sciatic Nerve: Histopathologic and Morphometric Studies, Int. J. Hyperthermia, 1994, vol. 10, No. 6, 845-855.

Webb, R.L. et al, Functional Identification of the Central Projections of Afferent Renal Nerves, Clin. and Exper.—Theory and Practice, Ag(Suppl.I), 47-57 (1987).

Weinstock, Marta et al, Renal Denervation Prevents Sodium Retention and Hypertension in Salt-Sensitive Rabbits with Genetic Baroreflex Impairment, Clinical Science (1996) 90, 287-293.

Wilcox, Josiah N., Scientific Basis Behind Renal Denervation for the Control of Hypertension, Medtronic, Inc., Dec. 2012, 38 pages.

Winternitz, Sherry R. et al, Role of the Renal Sympathetic Nerves in the Development and Maintenance of Hypertension in the Spontaneously Hypertensive Rat, Journal of Clinical Investigation, vol. 66 Nov. 1980, 971-978.

Wolf-Maier, Katharina et al, Hypertension Treatment and Control in Five European Countries, Canada, and the United States, Hypertension. 2004;43:10-17.

Worthley, Stephen G. et al, Renal Denervation: How Do You Measure Success?, presentation 28 pages; Jul. 30, 2013.

Wyss, J.M. et al, Sensory Denervation of the Kidney Attenuates Renovascular Hypertension in the Rat, Am J Physiol Heart Circ Physiol 250:H82-H86, 1986.

Yamada, Yutaka et al, Age-Related Changes in Muscle Sympathetic Nerve Activity in Essential Hypertension, Hypertension Journal of The American Heart Association, 1989;13:870-877.

Young, Robert R. et al, Reversible Block of Nerve Conduction by Ultrasound Ultrasonic Blocking of Nerve Fibers, Arch Neurol. 1961;4(1):83-89.

Jaff, Michael R. et al, Kidney Stenting Lowers Blood Pressure in Patients with Severe Hypertension; Catheterization and Cardiovascular Interventions; Published Online: Jun. 27, 2012 (DOI: 10.1002/ccd.24449); Print Issue Date: Sep. 2012. URL: http://onlinelibrary.wiley.com/doi/10.1002/ccd.24449/abstract.

Jain, Mudit K. et al, A Three-Dimensional Finite Element Model of Radiofrequency Ablation with Blood Flow and Its Experimental Validation, Annals of Biomedical Engineering, vol. 28, pp. 1075-1084, 2000.

Jais, Pierre et al, Efficacy and Safety of Septal and Left-Atrial Linear Ablation for Atrial Fibrillation, The American Journal of Cardiology, vol. 84 (9A), Nov. 1999, 139R-146R.

Janssen, Ben J.A. et al, Frequency-Dependent Modulation of Renal Blood Flow by Renal Nerve Activity in Conscious Rabbits, American Journal of Physiology, 1997, 273:R597-R608.

(56) References Cited

OTHER PUBLICATIONS

Janssen, Ben J.A. et al, Renal Nerves in Hypertension, Miner Electrolyte Metab 1989;15:74-82.
Jin, Yu et al, No Support for Renal Denervation in a Meta-Analysis, JACC vol. 62, No. 21, 2013 Correspondence Nov. 19/26, 2013:2029-30.
Kaltenbach, Benjamin et al, Renal Artery Stenosis After Renal Sympathetic Denervation, J Am Coll Cardiol. Dec. 25, 2012;60(25):2694-5.
Kaltenbach, Benjamin et al, Renal Sympathetic Denervation as Second-Line Therapy in Mild Resistant Hypertension: A Pilot Study, Catheterization and Cardiovascular Interventions 81:335-339 (2013).
Kamiya, Atsunori et al, Parallel Resetting of Arterial Baroreflex Control of Renal and Cardiac Sympathetic Nerve Activities During Upright Tilt in Rabbits, Am J Physiol Heart Circ Physiol 298: H1966-H1975, 2010.
Kandzari, David E. et al, Catheter-Based Renal Denervation for Resistant Hypertension: Rationale and Design of the Symplicity HTN-3 Trial, Clin. Cardiol. 35, 9, 528-535 (2012).
Kapural, Leonardo et al, Radiofrequency Ablation for Chronic Pain Control, Current Pain and Headache Reports 2001, 5:517-525.
Kassab, Salah et al, Renal Denervation Attenuates the Sodium Retention and Hypertension Associated with Obesity, Hypertension vol. 25, No. 4, Part 2 Apr. 1995.
Katholi, Richard E. et al, Decrease in Peripheral Sympathetic Nervous System Activity following Renal Denervation or Unclipping in the One-Kidney One-Clip Goldblatt Hypertensive Rat, The Journal of Clinical Investigation, Jan. 1982;69(1):55-62.
Katholi, Richard E. et al, Role of the Renal Nerves in the Pathogenesis of One-Kidney Renal Hypertension in the Rat, Hypertension. 1981;3:404-409.
Katholi, Richard E. et al, The Role of Renal Sympathetic Nerves in Hypertension: Has Percutaneous Renal Denervation Refocused Attention on Their Clinical Significance?; Progress in Cardiovascular Disease 52 (2009) 243-248.
Katritsis, Demosthenes et al, Recurrence of Left Atrium-Pulmonary Vein Conduction Following Successful Disconnection in Asymptomatic Patients, Europace (2004) 6, 425e432.
Killip III, Thomas, Oscillation of Blood Flow and Vascular Resistance During Mayer Waves, Circulation Research, vol. XI, Dec. 1962, 987-993.
Kingwell, Bronwyn A. et al, Assessment of Gain of Tachycardia and Bradycardia Responses of Cardiac Baroreflex, Am J Physiol Heart Circ Physiol 260:H1254-H1263, 1991.
Kirchheim, H. et al, Sympathetic Modulation of Renal Hemodynamics, Renin Release and Sodium Excretion, Klin Wochenschr (1989) 67: 858-864.
Klein, GE et al, Endovascular Treatment of Renal Artery Aneurysms with Conventional Non-Detachable Microcoils and Guglielmi Detachable Coils, Br J Urol. Jun. 1997; 79(6):852-860.
Knight, Eric L. et al, Predictors of Decreased Renal Function in Patients with Heart Failure During Angiotensin-Converting Enzyme Inhibitor Therapy: Results from the Studies of Left Ventricular Dysfunction (SOLVD), American Heart Journal, vol. 138, No. 5, Part 1, Nov. 1999, 849-855.
Koepke, John P. et al, Functions of the Renal Nerves, The Physiologist, vol. 28, No. 1, Feb. 1985, 47-52.
Kompanowska-Jezierska, Elzbieta et al, Early Effects of Renal Denervation in the Anaesthetised Rat: Natriuresis and Increased Cortical Blood Flow, Journal of Physiology (2001), 531.2, pp. 527-534.
Krum, Henry et al, Catheter-Based Renal Sympathetic Denervation for Resistant Hypertension: A Multicentre Safety and Proof-of-Principle Cohort Study, www.thelancet.com vol. 373 Apr. 11, 2009 1275-1281.
Krum, Henry et al, Device-Based Antihypertensive Therapy: Therapeutic Modulation of the Autonomic Nervous System, Circulation. 2011;123:209-215.
La Grange, Ronald G. et al, Selective Stimulation of Renal Nerves in the Anesthetized Dog: Effect on Renin Release During Controlled Changes in Renal Hemodynamics, Circulation Research, Journal of The American Heart Association, 1973;33:704-712.
Labeit, Alexander Michael et al, Changes in the Prevalence, Treatment and Control of Hypertension in Germany? A Clinical-Epidemiological Study of 50.000 Primary Care Patients, PLOS ONE, Dec. 2012, vol. 7, Issue 12, e52229, 1-11.
Labonte, Sylvain, Numerical Model for Radio-Frequency Ablation of the Endocardium and its Experimental Validation, IEEE Transactions on Biomedical Engineering, vol. 41, No. 2. Feb. 1994, 108-115.
Lambert, Gavin W. et al, Health-Related Quality of Life After Renal Denervation in Patients With Treatment-Resistant Hypertension, Hypertension. 2012;60:1479-1484.
Lee, Sang Joon et al, Ultrasonic Energy in Endoscopic Surgery, Yonsei Medical Journal, vol. 40, No. 6, pp. 545-549, 1999.
Leertouwer, Trude C. et al, In-Vitro Validation, with Histology, of Intravascular Ultrasound in Renal Arteries, Journal of Hypertension 1999, vol. 17 No. 2, 271-277.
Leishman, A.W.D., Hypertension—Treated and Untreated, British Medical Journal, May 1959, 1361-1368.
Leonard, Bridget L. et al, Differential Regulation of the Oscillations in Sympathetic Nerve Activity and Renal Blood Flow Following Volume Expansion, Autonomic Neuroscience: Basic and Clinical 83 (2000) 19-28.
Levin, Stephen, Ardian: Succeeding Where Drugs Fail Treating Hypertension in the Cath Lab, In Vivo: The Business & Medicine Report, vol. 27, No. 10, Nov. 2009.
Litynski, Grzegorz S., Kurt Semm and the Fight against Skepticism: Endoscopic Hemostasis, Laparoscopic Appendectomy, and Semm's Impact on the "Laparoscopic Revolution", JSLS. Jul.-Sep. 1998; 2(3): 309-313.
Lu, David S.K. et al, Effect of Vessel Size on Creation of Hepatic Radiofrequency Lesions in Pigs: Assessment of the "Heat Sink" Effect, American Journal of Radiology, 178, Jan. 2002, 47-51.
Luscher, Thomas F. et al, Renal Nerve Ablation After Symplicity HTN-3: Confused at the Higher Level?; European Heart Journal, doi:10.1093/eurheartj/ehu195; May 14, 2014.
Lustgarten, Daniel L. et al, Cryothermal Ablation: Mechanism of Tissue Injury and Current Experience in the Treatment of Tachyarrhythmias, Progress in Cardiovascular Diseases, vol. 41, No. 6 May/Jun. 1999: pp. 481-498.
Mahfoud, Felix et al, Expert Consensus Document from the European Society of Cardiology on Catheter-Based Renal Denervation, European Heart Journal, Jul. 2013;34(28):2149-57.
Mancia, Giuseppe et al, Sympathetic Activation in the Pathogenesis of Hypertension and Progression of Organ Damage, Hypertension Journal of The American Heart Association, 1999, 34:724-728.
McGahan, John P. et al, History of Ablation, Tumor Ablation, 2005, pp. 3-16.
Medtronic, Inc., J.P. Morgan Healthcare Conference, Corrected Transcript, Jan. 13, 2014, Factset:Callstreet, www.callstreet.com.
Medtronic, Inc., Medtronic Announces U.S. Renal Denervation Pivotal Trial Fails to Meet Primary Efficacy Endpoint While Meeting Primary Safety Endpoint, www.medtronic.com, Jan. 9, 2014.
Medtronic, Inc., RDN Therapy with the Symplicity Renal Denervation System, Procedure Fact Sheet, www.medtronic.com, 2011.
Medtronic, Inc., Renal Denervation (RDN) Novel Catheter-based Treatment for Hypertension, Symplicity RDN System Common Q&A, 2011.
Medtronic, Inc., Scientific Basis Behind Renal Denervation for the Control of Hypertension, Dec. 2012, http://www.icimeeting.com/2012/images/stories/PDF/1448_Wilcox_I_Mon.pdf.
Mehdirad, Ali et al, Temperature Controlled RF Ablation in Canine Ventricle and Coronary Sinus using 7 Fr or 5 Fr Ablation Electrodes, PACE, vol. 21, Jan. 1998, Part II, 316-321.
Meredith, I T et al, Exercise Training Lowers Resting Renal But Not Cardiac Sympathetic Activity in Humans; Hypertension Journal of The American Heart Association, 1991;18:575-582.
Michaelis, Lawrence L. et al, Effects of Renal Denervation and Renin Depletion on the Renal Responses to Intravascular Volume Expansion, Ann Surg. Mar. 1972; 175(3): 424-430.

(56) References Cited

OTHER PUBLICATIONS

Millard, F.C. et al, Renal Embolization for Ablation of Function in Renal Failure and Hypertension, Postgraduate Medical Journal (1989) 65, 729-734.
Moak, Jeffrey P. et al, Case Report: Pulmonary Vein Stenosis Following RF Ablation of Paroxysmal Atrial Fibrillation: Successful Treatment with Balloon Dilation, Journal of Interventional Cardiac Electrophysiology, Dec. 2000, 4, 4:621-631.
Mogil, Robert A. et al, Renal Innervation and Renin Activity in Salt Metabolism and Hypertension, American Journal of Physiology, vol. 216, No. 4, Apr. 1969, 693-697.
Morita, Hironobu et al, Neural Control of Urinary Sodium Excretion During Hypertonic NaCl Load in Conscious Rabbits: Role of Renal and Hepatic Nerves and Baroreceptors, Journal of the Autonomic Nervous System, 34 (1991) 157-170.
Morrissey, D.M. et al, Sympathectomy in the Treatment of Hypertension, The Lancet, Feb. 1953, 403-408.
Mortara, Andrea et al, Nonselective Beta-Adrenergic Blocking Agent, Carvedilol, Improves Arterial Baroflex Gain and Heart Rate Variability in Patients With Stable Chronic Heart Failure, Journal of the American College of Cardiology, vol. 36, No. 5, 2000, 1612-1618.
Moss, Jonathan, Interventional Radiology and Renal Denervation, Interventions, vol. 13, Issue 3, 2013.
Naghavi, Morteza et al, Thermography Basket Catheter: In Vivo Measurement of the Temperature of Atherosclerotic Plaques for Detection of Vulnerable Plaques, Catheterization and Cardiovascular Interventions 59:52-59 (2003).
Naidoo, N. et al, Thoracic Splanchnic Nerves: Implications for Splanchnic Denervation, Journal of Anatomy, Nov. 2001;199(Pt 5):585-590.
Nakagawa, A. et al, Selective Ablation of Porcine and Rabbit Liver Tissue Using Radiofrequency: Preclinical Study, European Surgical Research, 1999;31:371-379.
Nakagawa, Hiroshi et al, Inverse Relationship Between Electrode Size and Lesion Size During Radiofrequency Ablation With Active Electrode Cooling, Circulation. Aug. 4, 1998;98(5):458-465.
Nanni, Gregg S. et al, Control of Hypertension by Ethanol Renal Ablation, Radiology 148: 51-54, Jul. 1983.
Ndegwa, S., Catheter-Based Renal Denervation for Treatment-Resistant Hypertension [Issues in emerging health technologies issue 121]. Ottawa: Canadian Agency for Drugs and Technologies in Health; 2013.
Neutel, Joel M., Hypertension and Its Management: A Problem in Need of New Treatment Strategies, Journal of Renin-Angiotensin-Aldosterone System 2000 1: S10-S13.
Newcombe, C.P. et al, Sympathectomy for Hypertension, British Medical Journal, Jan. 1959, 142-144.
Ng, Fu Siong et al, Catheter Ablation of Atrial Fibrillation, Clinical Cardiology, 25, 384-394 (2002).
Norman, Roger A. et al, Role of the Renal Nerves in One-Kidney, One Clip Hypertension in Rats, Hypertension Journal of The American Heart Association, 1984;6:622-626.
Nozawa, Takashi et al, Effects of Long-Term Renal Sympathetic Denervation on Heart Failure After Myocardial Infarction in Rats, Heart Vessels (2002) 16:51-56.
O'Connor, Brian K. et al, Radiofrequency Ablation of a Posteroseptal Accessory Pathway via the Middle Cardiac Vein in a Six-Year-Old Child, PACE, vol. 20, Oct. 1997, Part 1, 2504-2507.
O'Hagen, Kathleen P. et al, Renal Denervation Decreases Blood Pressure in DOCA-Treated Miniature Swine With Established Hypertension, American Journal of Hypertension, 1990; 3:62-64.
Oliveira, Vera L.L. et al, Renal Denervation Normalizes Pressure and Baroreceptor Reflex in High Renin Hypertension in Conscious Rats, Hypertension vol. 19, No. 2 Feb. 1992, Supplement II, II-17-II-21.
Omran, Heyder et al, Echocardiographic Imaging of Coronary Sinus Diverticula and Middle Cardiac Veins in Patients with Preexcitation Syndrome: Impact—on Radiofrequency Catheter Ablation of Posteroseptal Accessory Pathways, PACE, vol. 18, Jun. 1995, 1236-1243.
Oparil, Suzanne et al, Renal Nerve Ablation: Emerging Role in Therapeutics; Blood Pressure, Oct. 2011, vol. 20, No. 5, pp. 253-255.
Oral, Hakan et al, Pulmonary Vein Isolation for Paroxysmal and Persistent Atrial Fibrillation, Circulation Journal of The American Heart Association, 2002;105:1077-1081.
Osborn, Jeffrey L. et al, Long-Term Increases in Renal Sympathetic Nerve Activity and Hypertension, Clinical and Experimental Pharmacology and Physiology (1997) 24,72-76.
Osborn, John W., The Sympathetic Nervous System and Long-Term Regulation of Arterial Pressure: What Are the Critical Questions?, Clinical and Experimental Pharmacology and Physiology (1997) 24, 68-71.
Ou, Baiqing et al, Baroreflex Sensitivity Predicts the Induction of Ventricular Arrhythmias by Cesium Chloride in Rabbits, Japanese Circulation Journal, 1999; 63: 783-788.
Oz, Mehmet, Pressure Relief, TIME Magazine, Monday, Jan. 9, 2012.
Page, Irvine H. et al, Mechanisms, Diagnosis and Treatment of Hypertension of Renal Vascular Origin, Annal of Internal Medicine, Aug. 1959, vol. 51, No. 2, 196-211.
Page, Irvine H. et al, Mechanisms, Diagnosis and Treatment of Hypertension of Renal Vascular Origin; Annals of Internal Medicine, Aug. 1959;51:196-211.
Page, Irvine H. et al, The Effect of Renal Denervation on the Level of Arterial Blood Pressure and Renal Function in Essential Hypertension, Journal of Clinical Investigation, 1935;14(1):27-30.
Page, Irvine H. et al, The Effects of Renal Denervation on Patients Suffering from Nephritis, J Clin Invest. 1935;14(4):443-458.
Page, Irvine H., The Effect of Renal Efficiency of Lowering Arterial Blood Pressure in Cases of Essential Hypertension and Nephritis, Journal of Clinical Investigation, Nov. 1934; 13(6): 909-915.
Page, Max, Section of Surgery, Discussion on the Surgical Treatment of Hypertension, Proceedings of the Royal Society of Medicine, vol. XLI, Feb. 1948, 359-372.
Papademetriou, Vasilios, Hypertension and the Simplicity Renal Denervation System, Scientific Background, www.medtronic.com, 2011.
Pappone, Carlo et al, Circumferential Radiofrequency Ablation of Pulmonary Vein Ostia: A New Anatomic Approach for Curing Atrial Fibrillation, Circulation, Journal of The American Heart Association, 2000;102:2619-2628.
Parati, Gianfranco et al, The Human Sympathetic Nervous System: Its Relevance in Hypertension and Heart Failure, European Heart Journal (2012) 33, 1058-1066.
Parmar, Arundhati, Analyst: Medtronic Will Likely Acquire Another Hypertension Therapy Firm, Medcity News, Apr. 27, 2012; 3:06 p.m.; medcitynews.com.
Pavlovich, Christian P. et al, Percutaneous Radio Requency Ablation of Small Renal Tumors: Initial Results; The Journal of Urology, vol. 167, Jan. 10-15, 2002.
Pearce, John A. et al, Blood Vessel Architectural Features and Their Effect on Thermal Phenomena, Critical Reviews, vol. CR75, Bellingham, WA: SPIE Optical Engineering Press; 2000, p. 231-277.
Peet, Max Minor, Hypertension and Its Surgical Treatment by Bilateral Supradiaphragmatic Splanchnicectomy, American Journal of Surgery, vol. 75, Issue 1, Jan. 1948, 48-68.
Perry, C. Bruce, Malignant Hypertension Cured by Unilateral Nephrectomy, British Heart Journal, Jul. 1945; 7(3): 139-142.
Persu, Alexandre et al, Renal Denervation: Ultima Ratio or Standard in Treatment-Resistant Hypertension, Hypertension Journal of The American Heart Association, Sep. 2012;60(3):596-606.
Peterson, Helen Hogh et al, Lesion Dimensions During Temperature-Controlled Radiofrequency Catheter Ablation of Left Ventricular Porcine Myocardium Impact of Ablation Site, Electrode Size, and Convective Cooling, Circulation Journal of The American Heart Association, 1999;99:319-325.

(56) References Cited

OTHER PUBLICATIONS

Plouin, Pierre-Francois et al, Blood Pressure Outcome of Angioplasty in Atherosclerotic Renal Artery Stenosis A Randomized Trial, Hypertension Journal of The American Heart Association, 1998;31:823-829.
Poutasse, Eugene F., Surgical Treatment of Renal Hypertension, American Journal of Surgery, vol. 107, Jan. 1964, 97-103.
Pugsley, M.K. et al, The Vascular System an Overview of Structure and Function, Journal of Pharmacological and Toxicological Methods 44 (2000) 333-340.
Putney, John Paul, Are Secondary Considerations Still "Secondary"?:An Examination of Objective Indicia of Nonobviousness Five Years After KSR, Intellectual Property Brief, vol. 4, Issue 2, Article 5, 2012, 45-59.
Ramsay, Lawrence E. et al, Blood Pressure Response to Percutaneous Transluminal Angioplasty for Renovascular Hypertension: An Overview of Published Series; British Medical Journal Mar. 3, 1990; 300(6724): 569-572.
Rippy, Marian K. et al, Catheter-Based Renal Sympathetic Denervation: Chronic Preclinical Evidence for Renal Artery Safety, Clin Res Cardiol (2011) 100:1095-1101.
Ritz, Eberhard, New Approaches to Pathogenesis and Management of Hypertension, Clin J Am Soc Nephrol 4: 1886-1891, 2009.
Dibona, Gerald F., Renal Innervation and Denervation: Lessons from Renal Transplantation Reconsidered, Artificial Organs, vol. 11, No. 6, 1987, 457-462.
Dibona, Gerald F., Role of the Renal Nerves in Renal Sodium Retention and Edema Formation, Trans Am Clin Climatol Assoc. 1990; 101: 38-45.
Dibona, Gerald F., Sympathetic Nervous System and Hypertension, Hypertension Journal of The American Heart Association, 2013; 61: 556-560.
Dibona, Gerald F., Sympathetic Nervous System and the Kidney in Hypertension, Curr Opin Nephrol Hypertens. Mar. 2002;11(2):197-200.
Dibona, Gerald F., The Sympathetic Nervous System and Hypertension, Hypertension Journal of The American Heart Association, Vo. 43, Feb. 2004, 147-150.
Doumas, Michael et al, Interventional Management of Resistant Hypertension, The Lancet, vol. 373, Apr. 11, 2009, pp. 1228-1230.
Dubuc, Marc et al, Feasibility of Cardiac Cryoablation Using a Transvenous Steerable Electrode Catheter, Journal of Interventional Cardiac Electrophysiology, 1998, 2: 285-292.
Elmula, Fadl et al, Renal Sympathetic Denervation in Patients With Treatment-Resistant Hypertension After Witnessed Intake of Medication Before Qualifying Ambulatory Blood Pressure, Hypertension. 2013;62:526-532.
Esler, M. et al, Sympathetic Nerve Activity and Neurotransmitter Release in Humans: Translation from Pathophysiology into Clinical Practice, Scandinavian Physiological Society, 2003, 177, 275-284.
Esler, Murray D. et al, Renal Sympathetic Denervation in Patients with Treatment-Resistant Hypertension (The Symplicity HTN-2 Trial): A Randomised Controlled Trial, Lancet, 2010; 376:1903-1909.
Esler, Murray et al, Assessment of Human Sympathetic Nervous System Activity from Measurements of Norepinephrine Turnover, Hypertension Journal of The American Heart Association, vol. 11, No. 1, Jan. 1988, 3-20.
Evelyn, Kenneth A. et al, Effect of Thoracolumbar Sympathectomy on the Clinical Course of Primary (Essential) Hypertension, American Journal of Medicine, Feb. 1960, 188-221.
Freyberg, R. H. et al, The Effect on the Kidney of Bilateral Splanchnicectomy in Patients with Hypertension, The Journal of Clinical Investigation, vol. 16, Issue 1, Jan. 1937, 49-65.
Gafoor, Sameer et al, Nonresponders to Renal Denervation for Resistant Hypertension, Endovascular Today, Oct. 2013, 63-70.
Garel, L. et al, Fatal Outcome After Ethanol Renal Ablation in Child with End-Stage Kidneys; AJR 146:593-594, Mar. 1986.
Gazdar, A. F. et al, Neural Degeneration and Regeneration in Human Renal Transplants, The New England Journal of Medicine, vol. 238, No. 5, Jul. 1970, 222-224.
Goldberg, Michael R. et al, Reconstructive Vascular Surgery for Renovascular Hypertension, Can Med Assoc J. Feb. 2, 1974;110(3):275-80.
Golwyn, Daniel H. et al, Percutaneous Transcatheter Renal Ablation with Absolute Ethanol for Uncontrolled Hypertension or Nephrotic Syndrome: Results in 11 Patients with End-Stage Renal Disease, Journal of Vascular and Interventional Radiology, Jul.-Aug. 1997, vol. 8, No. 4, 527-533.
Gorisch, Wolfram et al, Heat-Induced Contraction of Blood Vessels, Lasers in Surgery and Medicine 2:1-13 (1982).
Grassi, Guido et al, Baroreflex Control of Sympathetic Nerve Activity in Essential and Secondary Hypertension, Hypertension Journal of The American Heart Association, 1998;31:68-72.
Grassi, Guido et al, Dissociation Between Muscle and Skin Sympathetic Nerve Activity in Essential Hypertension, Obesity, and Congestive Heart Failure, Hypertension. 1998;31:64-67.
Grimson, Keith S. et al, Results of Treatment of Patients with Hypertension by Total Thoracic and Partial to Total Lumbar Sympathectomy, Splanchnicectomy and Celiac Ganglionectomy, Annals of Surgery, Jun. 1949, vol. 129, No. 6, 850-871.
Grimson, Keith S. et al, Total Thoracic and Partial to Total Lumbar Sympathectomy, Splanchnicectomy and Celiac Ganglionectomy for Hypertension, Annals of Surgery, Oct. 1953, vol. 138, No. 4, 532-547.
Grimson, Keith S., Total Thoracic and Partial to Total Lumbar Sympathectomy and Celiac Ganglionectomy in the Treatment of Hypertension, Annals of Surgery, Oct. 1941, vol. 114, No. 4, 753-775.
Guyton, Arthur C., Blood Pressure Control Special Role of the Kidneys and Body Fluids, Science, vol. 252, Jun. 1991, 1813-1816.
Hafkenschiel, Joseph H. et al, Primary Hypertension Survey of the Survival of Patients with Established Diastolic Hypertension After Ten Years of Medical and Surgical Treatment, The American Journal of Cardiology, vol. 16, Jul. 1965, 61-66.
Hafkenschiel, Joseph H. et al, The Surgical Treatment of Hypertension with Particular Reference to Andrenalectomy and Sympathectomy, Transactions. American College of Cardiology, vol. 5, Dec. 1955, pp. 107-112.
Hall, J.E. et al, Role of Sympathetic Nervous System and Neuropeptides in Obesity Hypertension, Brazilian Journal of Medical and Biological Research, 2000, 33:605-618.
Hall, John E., The Kidney, Hypertension, and Obesity, Hypertension. 2003;41:625-633.
Hall, Winthrop H. et al, Combined Embolization and Percutaneous Radiofrequency Ablation of a Solid Renal Tumor, American Journal of Roentgenology, 174, Jun. 2000, 1592-1594.
Hamm, Christian et al, Confluence, Issue eight, Apr. 2014.
Han, Young-Min et al, Renal Artery Embolization with Diluted Hot Contrast Medium: An Experimental Study, Journal of Vascular and Interventional Radiology, Jul. 2001;12(7):862-868.
Hansen, Jesper Melchoir et al, The Transplanted Human Kidney Does Not Achieve Functional Reinnervation, Clinical Science, (1994) 87, 13-20.
Heuer, George J., The Surgical Treatment of Essential Hypertension, Annals of Surgery, Oct. 1936, vol. 104, No. 3, 771-786.
Hinton, J. William, End Results of Thoracolumbar Sympathectomy for Advanced Essential Hypertension, The Bulletin, Apr. 1948, 239-252.
Holmer, Stephan et al, Role of Renal Nerves for the Expression of Renin in Adult Rat Kidney, The American Journal of Physiology, May 1994;266(5 Pt 2):F738-F745.
Hoobler, S.W. et al, The Effects of Splanchnicectomy on the Blood Pressure in Hypertension, Circulation Journal of The American Heart Association, vol. IV, Aug. 1951, 173-183.
Hoppe, Uta C. et al, Minimally Invasive System for Baroreflex Activation Therapy Chronically Lowers Blood Pressure with Pacemaker-like Safety Profile: Results from the Barostim Neo Ttrial, J Am Soc Hypertens. Jul.-Aug. 2012;6(4):270-6.
Howard, James P. et al, Size of Blood Pressure Reduction from Renal Denervation: Insights from Meta-Analysis of Antihyperten- (56) References Cited

OTHER PUBLICATIONS sive Drug Trials of 4121 Patients with Focus on Trial Design: the CONVERGE Report, Heart 2013;0:1-9.
Howard, James P. et al, Unintentional Overestimation of an Expected Antihypertensive Effect in Drug and Device Trials: Mechanisms and Solutions, International Journal of Cardiology, vol. 172, Issue 1, Mar. 1, 2014, pp. 29-35.
Howell, Marcus H. et al, Tandem Stenting of Crossed Renal Arteries with Ostial Stenosis, Tex Heart Inst J. 2000; 27(2): 166-169.
Hoye, Neil A. et al, Endovascular Renal Denervation: A Novel Sympatholytic with Relevance to Chronic Kidney Disease, Clinical Kidney Journal Advance Access, (2013) 0: 1-8.
Huang, Shoei K. Stephen et al, Radiofrequency Catheter Ablation of Cardiac Arrhythmias, Basic Concepts and Clinical Applications, Wiley-Blackwell, Jun. 2000, 1-12.
Huang, Wann-Chu, Renal Denervation Prevents and Reverses Hyperinsulinemia-Induced Hypertension in Rats, Hypertension Journal of the American Heart Association, 1998;32:249-254.
Humpreys, Michael H., Renal Nerves and CKD: Is Renal Denervation the Answer?, Journal of the American Socity of Nephrology, 2012, 23: 1-3.
International Search Report and Written Opinion for Application No. PCT/US2010/054637 dated Jan. 3, 2011.
International Search Report and Written Opinion for Application No. PCT/US2010/054684 dated Jan. 10, 2011.
Irigoyen, M.C.C. et al, Baroreflex Control of Sympathetic Activity in Experimental Hypertension, Brazilian Journal of Medical and Biological Research, (1998) 31: 1213-1220.
Izzo, Jr, Joseph L. et al, The Sympathetic Nervous System and Baroreflexes in Hypertension and Hypotension, Hypertension Reports 1999, 3:254-263.
Jackman, Warren M. et al, Catheter Ablation of Arrhythmias, Proposed Anatomy and Catheter Ablation of Epicardial Posteroseptal and Left Posterior Accessory AV Pathways (Chapter 16), 2002, Futura Publishing Company, Inc., 321-343.
Zazgornik, Jan et al, Bilateral Nephrectomy: The Best, but Often Overlooked, Treatment for Refractory Hypertension in Hemodialysis Patients, AJH 1998; 11:1364-1370.
Abboud, Francois M., The Sympathetic System in Hypertension, State-of-the-Art Review, Hypertension Journal of the American Heart Association, Hypertension 4 (suppl II):II-208-II-225, 1982.
Allen, Edgar V., Sympathectomy for Essential Hypertension, Circulation Journal of the American Heart Association, vol. VI, Jul. 1952, 131-140.
Anderson, Erling A. et al, Elevated Sympathetic Nerve Activity in Borderline Hypertensive Humans, Evidence From Direct Intraneural Recordings, Hypertension Journal of the American Heart Association, vol. 14, No. 2, Aug. 1989, 177-183.
Ardian, Inc., Ardian(R) Receives 2010 EuroPCR Innovation Award and Demonstrates Further Durability of Renal Denervation Treatment for Hypertension, PR Newswire, Jun. 3, 2010.
Arentz, Thomas et al, Feasibility and Safety of Pulmonary Vein Isolation Using a New Mapping and Navigation System in Patients with Refractory Atrial Fibrillation, Circulation Journal of the American Heart Association, Nov. 18, 2003, 2484-2490.
Badoer, Emilio et al, Cardiac Afferents Play the Dominant Role in Renal Nerve Inhibition Elicited by Volume Expansion in the Rabbit, American Journal of Physiology, 1998, R383-R388.
Bakris, George L. et al, Baroreflex Activation Therapy Provides Durable Benefit in Patients with Resistant Hypertension: Results of Long-Term Follow-up in the Rheos Pivotal Trial, J Am Soc Hypertens. Mar.-Apr. 2012;6 (2):152-8.
Bao, Gang et al, Blood Pressure Response to Chronic Episodic Hypoxia: Role of the Sympathetic Nervous System, American Journal of Physiology, 1997, 95-101.
Barajas, Luciano et al, Anatomy of the Renal Innervation: Intrarenal Aspects and Ganglia of Origin, Canadian Journal of Physiology and Pharmacology, vol. 70, No. 5, May 1992, 735-749.

Barajas, Luciano et al, Monoaminergic Innervation of the Rat Kidney: A Quantitative Study, American Journal of Physiology, vol. 259, No. 3, Sep. 1990, F503-F511.
Bardram, Linda et al, Late Results After Surgical Treatment of Renovascular Hypertension, A Follow-up Study of 122 Patients 2-18 Years After Surgery, Annals of Surgery, vol. 201, No. 2, Feb. 1985, 219-224.
Bello-Reuss, Elsa et al, Effect of Renal Sympathetic Nerve Stimulation on Proximal Water and Sodium Reabsorption, The Journal of Clinical Investigation, vol. 57, Apr. 1976, 1104-1107.
Bello-Reuss, Elsa et al, Effects of Acute Unilateral Renal Denervation in the Rat, The Journal of Clinical Investigation, vol. 56, Jul. 1975, 208-217.
Benito, Fernando et al, Radiofrequency Catheter Ablation of Accessory Pathways in Infants, Heart, 1997, 78, 160-162.
Bernardi, Luciano et al, Influence of Type of Surgery on the Occurrence of Parasympathetic Reinnervation After Cardiac Transplantation, Circulation Journal of The American Heart Association, Apr. 14, 1998;97(14):1368-74.
Bertog, Stefan C. et al, Renal Denervation for Hypertension, JACC: Cardiovascular Interventions, vol. 5, No. 3, Mar. 2012, 249-258.
Bertram, Harald et al, Coronary Artery Stenosis After Radiofrequency Catheter Ablation of Accessory Atrioventricular Pathways in Children with Ebstein's Malformation, Circulation Journal of the American Heart Association, 2001, 538-543.
Blankestijn, Peter J. et al, Renal Denervation: Potential Impact on Hypertension in Kidney Disease?, Nephrol Dial Transplant (2011) 0: 1-3.
Blankestijn, Peter J. et al, Sympathetic Overactivity in Renal Failure Controlled by ACE Inhibition: Clinical Significance, Nephrol Dial Transplant, 2000, 15, 755-758.
Blum, Ulrich et al, Treatment of Ostial Renal-Artery Stenoses with Vascular Endoprostheses After Unsuccessful Balloon Angioplasty, The New England Journal of Medicine, vol. 336, No. 7, Feb. 1997, 459-465.
Brinkmann, Julia et al, Catheter-Based Renal Nerve Ablation and Centrally Generated Sympathetic Activity in Difficult-to-Control Hypertensive Patients Prospective Case Series, Hypertension. 2012;60:1485-1490.
Brookes, Linda et al, Renal Denervation: Is Reality Meeting Expectations?, An Interview with Michel Azizi, MD, PhD, Medscape, Jan. 7, 2013.
Bunte, Matthew C. et al, Endovascular Treatment of Resistant and Uncontrolled Hypertension, JACC: Cardiovascular Interventions, vol. 6, No. 1, 2013, 1-9.
Calleary, Hickey D. et al, Pre-Transplant Bilateral Native Nephrectomy for Medically Refractory Hypertension, The Irish Medical Journal, Jul.-Aug. 2001;94(7):214-6.
Callens, David J. et al, Narrowing of the Superior Vena Cava-Right Atrium Junction During Radiofrequency Catheter Ablation for Inappropriate Sinus Tachycardia: Analysis with Intracardiac Echocardiography, Journal of the American College of Cardiology, vol. 33, No. 6, 1999, 1667-1670.
Campese, V.M., Is Hypertension in Chronic Renal Failure Neurogenic in Nature?, Nephrol Dial Transplant, 1994, 9: 741-742.
Campese, Vito M. et al, Neurogenic Factors in Renal Hypertension, Current Hypertension Reports, 2002 4: 256-260.
Campese, Vito M. et al, Renal Afferent Denervation Prevents Hypertension in Rats With Chronic Renal Failure, Hypertension, 1995, 25, 878-882.
Campese, Vito M. et al, Renal Afferent Denervation Prevents the Progression of Renal Disease in the Renal Ablation Model of Chronic Renal Failure in Rat, American Journal of Kidney Disease, vol. 26, No. 5, Nov. 1995, 861-865.
Campese, Vito M., Interventional Hypertension: A New Hope or a New Hype? The Need to Redefine Resistant Hypertension, J Hypertens. Nov. 2013;31(11):2118-21.
Canadian Agency for Drugs and Technologies in Health, Catheter-Based Renal Denervation for Treatment-Resistant Hypertension; Issues in Emerging Health Technologies, Issue 121, Mar. 2013.
Carlstedt, Thomas et al, Regrowth of Lesioned Dorsal Root Nerve Fibers into the Spinal Cord of Neonatal Rats, Neuroscience Letters Feb. 10, 1987;74(1):14-8.

(56) References Cited

OTHER PUBLICATIONS

Chabanier, H. et al, On the Decapsulation and Neurectomy of the Kidnesy in Permanent Hypertensive States, The Medical Press, Feb. 22, 1936, No. 16, 307-310.

Ciccone, C D et al, Effects of Acute Renal Denervation on Kidney Function in Deoxycorticosterone Acetate-Hypertensive Swine, Hypertension Journal of the American Heart Association, Oct. 1986, vol. 8, No. 10, 925-931.

Ciriello, John et al, Renal Afferents and Hypertension, Current Hypertension Reports 2002, 4:136-142.

Converse, Richard L. et al, Sympathetic Overactivity in Patients with Chronic Renal Failure, The New England Journal of Medicine, vol. 327, No. 27, 1992, 1912-1918.

Crile, George, The Clinical Results of Celiac Ganglionectomy in the Treatment of Essential Hypertension, Annals of Surgery, Jun. 1938; 107(6): 909-916.

Cruickshank, J.M., Beta-Blockers Continue to Surprise Us, European Heart Journal (2000) 21, 354-364.

Curtis, John J. et al, Surgical Therapy for Persistent Hypertension After Renal Transplantation, Transplantation, vol. 31, No. 2, 1981, 125-128.

Dailey, U.G., Surgical Treatment of Hypertension: A Review—Part II, Journal of the National Medical Association, May 1948, vol. 40, No. 3., 113-116.

Dailey, U.G., Surgical Treatment of Hypertension: A Review—Part III, Journal of the National Medical Association, Jul. 1948, vol. 40, No. 4, 160-162.

Dailey, U.G., The Surgical Treatment of Hypertension: A Review, Journal of the National Medical Association, Mar. 1948, vol. 40, No. 2, 76-79.

Davis, Mark I. et al, Effectiveness of Renal Denervation Therapy for Resistant Hypertension A Systematic Review and Meta-Analysis, Journal of the American College of Cardiology, vol. 62, No. 3, 2013, 231-241.

De Wardener, H.E., The Hypothalamus and Hypertension, Physiological Reviews,vol. 81, No. 4, Oct. 2001.

Dequattro V. et al, The Sympathetic Nervous System: The Muse of Primary Hypertension, Journal of Human Hypertension, 2002, 16 (Supp) 1), S64-S69.

Dibona, Gerald F. et al, Neural Control of Renal Function, Physiological Reviews, vol. 77, No. 1, Jan. 1997, 75-197.

Dibona, Gerald F. et al, Translational Medicine: The Antihypertensive Effect of Renal Denervation, America! Journal of Physiology, 2010, 298, R245-R253.

Dibona, Gerald F., Neural Control of Renal Function: Cardiovascular Implications, Hypertension Journal of the American Heart Association, vol. 13, No. 6, Part 1, Jun. 1989, 539-548.

Dibona, Gerald F., Neural Control of the Kidney: Functionally Specific Renal Sympathetic Nerve Fibers, American Journal of Physiology, 2000, 279, R1517-R1524.

Dibona, Gerald F., Neural Control of the Kidney: Past, Present, and Future, Hypertension Journal of The American Heart Association, vol. 41, Mar. 2003, Part II, 621-624.

\* cited by examiner

HIGH STRENGTH ELECTRODE ASSEMBLY FOR CATHETER SYSTEM INCLUDING NOVEL ELECTRODE

CROSS-REFERENCE TO RELATED APPLICATIONS

This application claims priority to provisional application Ser. No. 61/895,183, filed Oct. 24, 2013, the entire specification of which is incorporated herein.

BACKGROUND OF THE DISCLOSURE

A. Field of the Disclosure

The present disclosure relates generally to a catheter system for use in a human body. More particularly, the present disclosure relates to a multi-electrode catheter system, and even more particularly to an electrode assembly for a multi-electrode catheter system that includes high strength, low profile struts that include one or more low profile electrodes.

B. Background Art

Catheter systems are well known in the art for use in medical procedures, such as diagnostic, therapeutic and ablative procedures. Typical catheter systems generally include an elongate catheter extending from a handle. A physician manipulates the catheter through the patient's vasculature to an intended site within the patient, generally through a guide catheter or the like. Because the vasculature can be tortuous, it is desirable to minimize the size of the components as much as possible. The catheter typically carries one or more working components, such as electrodes or other diagnostic, therapeutic or ablative devices for carrying out the procedures. One or more controls or actuators may be provided on the handle for selectively adjusting one or more characteristics of the working components.

One particular example of a multi-electrode catheter system is an ablative catheter system in which the working component is a multi-electrode component carried at the distal end of a flexible catheter. A control or pull wire extends within the catheter from the multi-electrode component to the handle to operatively connect the multi-electrode component to an actuator on the handle. Manipulating the actuator acts on the control wire to configure the multi-electrode component into a desired configuration for carrying out the ablative procedure. For example, in one such ablative catheter system made by St. Jude Medical, Inc. under the trade name ENLIGHTN™, the multi-electrode component is an electrode assembly in the general form of a basket. Upon locating the electrode basket at a desired location within the patient, manipulating the actuator associated with the handle pulls on the control wire to reconfigure the electrode basket from a collapsed configuration to an expanded configuration in which the electrodes are intended to be in apposition with a surface, such as an arterial wall of the patient. It is thus desirable to facilitate apposition of as many of the electrodes of the electrode basket as possible against the arterial wall of the patient when the electrode basket is expanded to achieve optimal performance of the multi-electrode catheter system.

BRIEF SUMMARY OF THE DISCLOSURE

In one embodiment, the present disclosure is directed to an electrode assembly having a proximal end and a distal end. The electrode assembly comprises at least one strut having a proximal end and a distal end and extending from the proximal end to the distal end of the electrode assembly. The at least one strut has a major width:thickness ratio of from about 2.571 to about 7.750, a minor width on the proximal and distal end of from about 0.010 inches to about 0.015 inches and an $A_f$ of from $-10°$ C. to $25°$ C. The at least one strut has a curved cross section.

In another embodiment, the present disclosure is directed to an electrode assembly strut for an electrode assembly. The strut has a major width:thickness ratio of from about 2.571 to about 7.750, a minor width on the proximal and distal end of from about 0.010 inches to about 0.015 inches and an $A_f$ of from $-10°$ C. to $25°$ C. The strut has a curved cross section.

In another embodiment, the present disclosure is directed to an electrode assembly having a proximal end and a distal end. The electrode assembly comprises at least one strut extending from the proximal end to the distal end of the electrode assembly, and the at least one strut includes at least one electrode. The at least one electrode has a height of no more than 0.031 inches and a width of no more than 0.067 inches such that the electrode assembly is sized and configured to be inserted into a 6 French guide catheter.

In another embodiment, the present disclosure is directed to an electrode assembly electrode. The electrode comprises a height of no more than 0.031 inches and a width of no more than 0.067 inches.

In another embodiment, the present disclosure is directed to an electrode assembly having a proximal end and a distal end. The electrode assembly comprises at least one strut having a proximal end and a distal end and extending from the proximal end to the distal end of the electrode assembly. The electrode assembly additionally includes at least one electrode. The at least one strut has a major width:thickness ratio of from about 2.571 to about 7.750, a minor width on the proximal and distal end of from about 0.010 inches to about 0.015 inches and an $A_f$ of from $-10°$ C. to $25°$ C. The at least one strut has a curved cross section. The electrode comprises a height of no more than 0.031 inches and a width of no more than 0.067 inches.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

The present disclosure provides electrode assemblies suitable for use in the human vasculature for known medical procedures, such as renal ablation procedures. The electrode assemblies of the present disclosure are sized and configured for easy insertion into, and use with, a guide catheter. Suitable guide catheters may be of many sizes, and one specific size is a 6 French guide catheter that typically has an inner diameter of about 0.070 inches (about 0.178 centimeters). The electrode assemblies generally include a plurality of struts that allow the electrode assembly to expand in diameter when compressed along its long axis. The struts of the electrode assembly are designed to provide a significantly lower profile for the electrode assembly when in a collapsed configuration as compared to conventional electrode assemblies, while providing superior strength to resist radial compression of the electrode assembly when the electrode assembly is in an expanded conformation. In many embodiments, the struts of the electrode assemblies include a polymer layer, such as a coextruded polymer layer, disposed thereon to tailor the desired strut rigidity and strength and to reduce friction upon movement of the electrode assembly inside of a guide catheter or similar device.

Additionally, the present disclosure provides novel low profile electrodes for positioning on the electrode assembly struts and for use in the electrode assembly. The electrodes are sized, shaped, and configured such that when the electrode assembly is in a collapsed conformation, the overall profile of the electrode assembly is reduced as compared to conventional electrode assemblies, such that the electrode assembly may be easily passed through reduced diameter guide catheters and the like with reduced drag and friction. Specifically, the electrodes are designed to include a concave electrode underside in combination with rounded underside corners and a reduced height that ultimately reduce the overall profile of the electrode on the electrode assembly strut without compromising performance and reliability.

Figure 1:
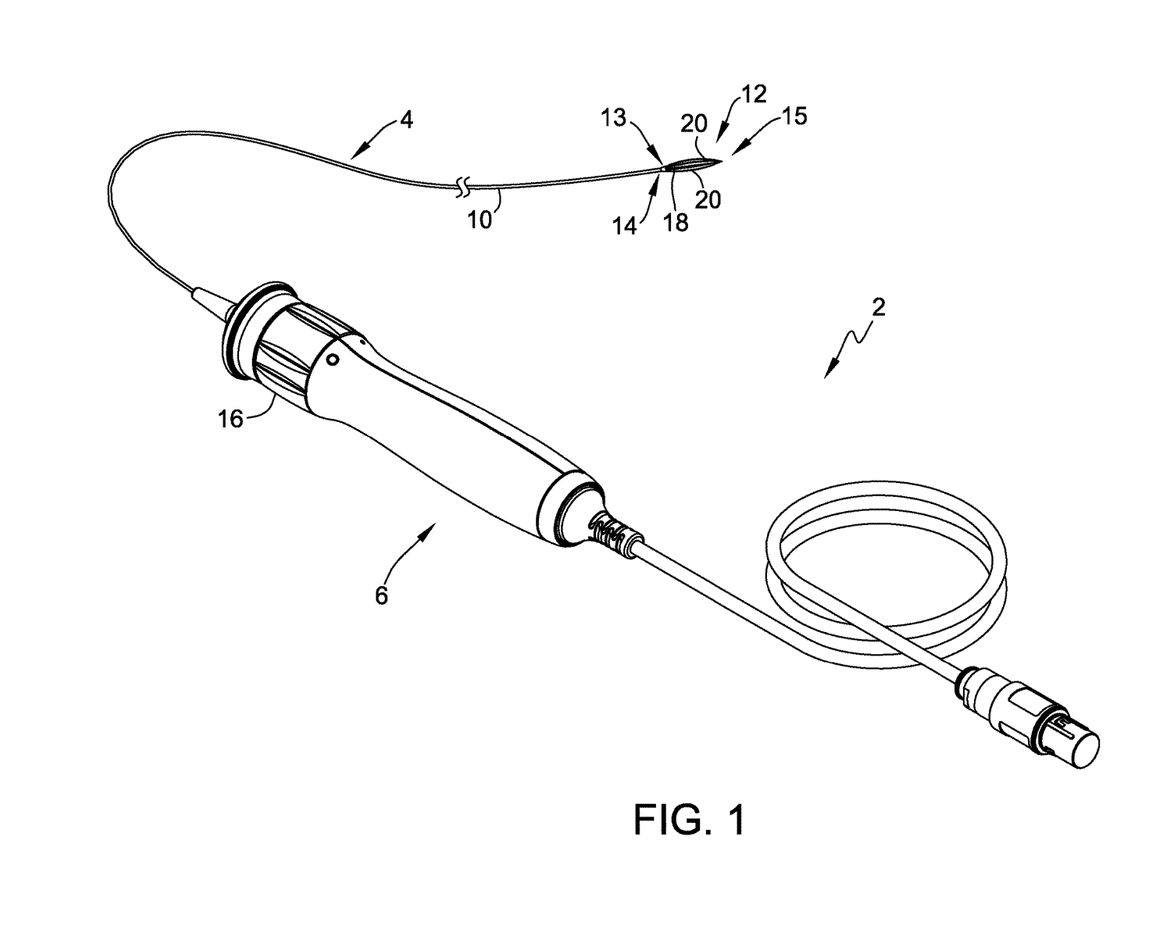
FIG. 1 is a perspective view of one embodiment of a catheter system including a handle, a catheter and an electrode assembly having multiple electrodes, with the electrode assembly being in a collapsed configuration.
Figure 2:
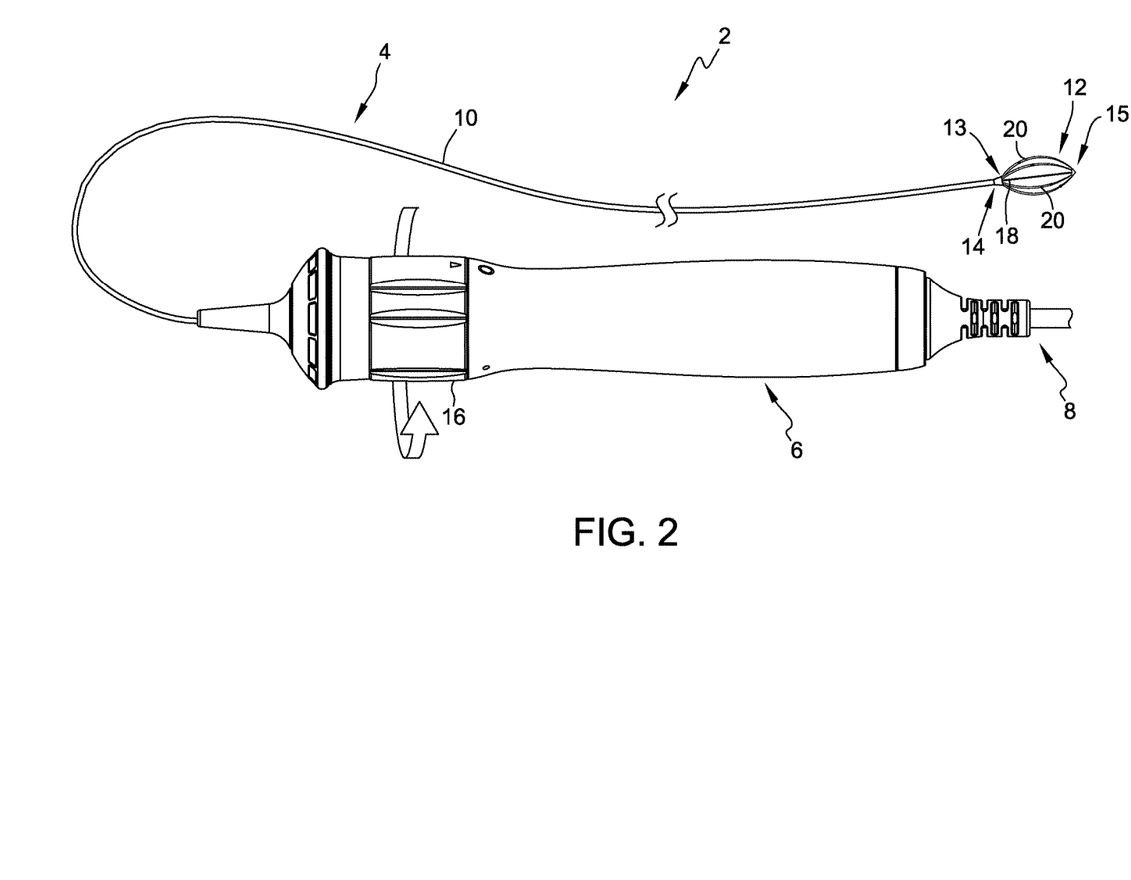
FIG. 2 is a side elevation of the catheter system of FIG. 1, with the electrode assembly being in an expanded configuration.

Referring now to the drawings, and in particular to FIGS. 1 and 2, a conventional catheter system 2 is shown by way of background and reference. Catheter system 2 includes a flexible catheter 4, a handle 6 to which flexible catheter 4 is connected, and a conductor assembly 8 for electrically connecting catheter system 2 to a suitable power supply (not shown). As one example, catheter system 2 illustrated and described herein is suitably constructed for use as an ablation system, such as a renal or heart ablation system. More particularly, illustrated catheter system 2 is a multi-electrode renal denervation system. One example of such a catheter system 2 is currently made by St. Jude Medical, Inc. under the trade name ENLIGHTN™. General operation of a multi-electrode renal denervation system is known to those of skill in the art and is not described further herein except to the extent necessary to describe the present embodiments. It is also understood that catheter system 2 may be used for any other suitable treatment or purpose without departing from the scope of this disclosure. Additionally, while catheter system 2 is illustrated and described herein as including flexible catheter 4, catheter system 2 may further include other components used, for example, to guide flexible catheter 4 into the patient—such as, without limitation, a relatively more rigid guide catheter (not shown) or guide wire (not shown).

Flexible catheter 4 includes an elongate, flexible hollow shaft 10 connected to handle 6 at or near a proximal or rear end of the catheter shaft (not shown because it is hidden by a connector at the front end of handle 6), and an electrode assembly 12 disposed at or near a distal or front end 14 of flexible hollow shaft 10. Electrode assembly 12 includes proximal end 13 and distal end 15. It is understood, however, that electrode assembly 12 may be disposed anywhere along flexible hollow catheter shaft 10 intermediate the proximal end and the distal end 14 thereof without departing from the scope of this disclosure. As used herein, the terms proximal and front, and distal and rear, are used with reference to the orientation of catheter system 2 illustrated in the various drawings and for the purpose of describing the various embodiments set forth herein, and are not intended as limiting the catheter system and related components to having any particular orientation upon assembly or during operation thereof. In particular, the terms proximal and rear refer to a longitudinal position that is relatively nearer to handle 6 while the terms distal and front refer to a longitudinal position that is relatively farther from handle 6.

Illustrated electrode assembly 12 is in the form of what may be referred to as an electrode basket and includes struts 20, and is suitably configurable between a collapsed configuration (FIG. 1) for maneuvering and positioning the electrode assembly in the patient, and an expanded configuration (FIG. 2) for operation of the electrode assembly to perform a desired procedure such as an ablation procedure. An annular (e.g., ring-shaped) actuator 16 is mounted on handle 6 for rotation relative thereto and is operatively connected to electrode assembly 12 for selectively configuring the electrode assembly between its collapsed and expanded configurations. It is understood that another suitable actuator (e.g., slide, push button, lever, etc.) may be used instead of rotating actuator 16 to selectively configure electrode assembly 12 without departing from the scope of this disclosure. In some embodiments, electrode assembly 12 may be selectively adjustable between an infinite number of configurations (e.g., degrees of expansion) between its collapsed and expanded configurations using actuator 16.

A control line, such as a suitable cable or pull wire 18, extends from electrode assembly 12 within hollow catheter shaft 10 and into the handle 6 for operative connection with the actuator to thereby operatively connect the actuator 16 with electrode assembly 12. In some embodiments two or more pull wires, cables or other suitable control lines or tubes may be used for selectively configuring electrode assembly 12. It is also understood that control line 18 may be any suitable control line other than a pull wire, such as a cable, string, tie, compression member or other suitable control to operatively connect electrode assembly 12 to actuator 16. A suitable electrical wire bundle (not shown) also extends through hollow catheter shaft 10 from handle 6 to electrode assembly 12 to deliver power to, and receive feedback from, electrode assembly 12.

As noted herein, the electrode assembly struts of the present disclosure are designed such that upon use in the electrode assembly, they exhibit increased radial strength (and hence, increased resistance to radial compression when in an expanded configuration), while having a relatively low profile such that upon the collapse of the electrode assembly, the electrode assembly may be inserted and moved easily within a reduced diameter catheter system, such as a 6 French size catheter.

Figure 3:
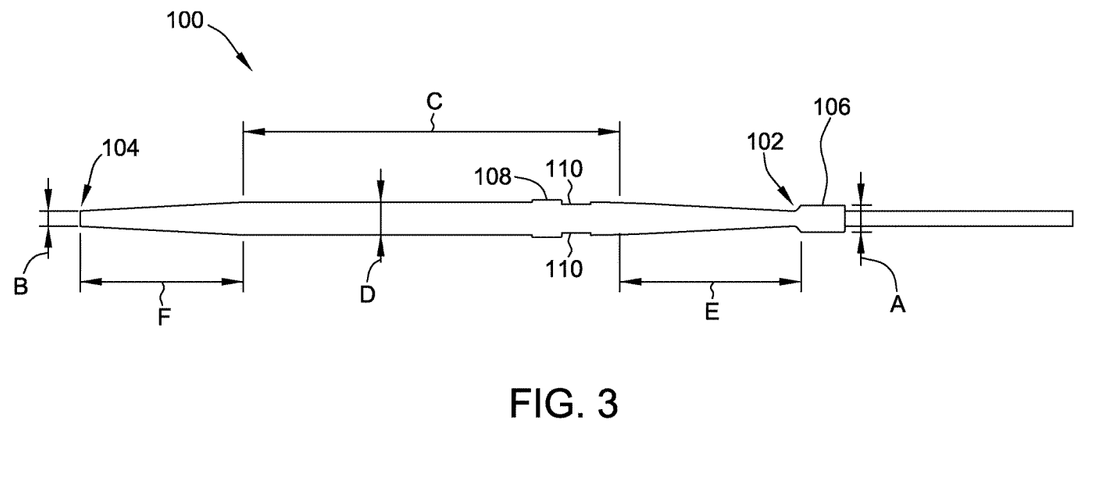
FIG. 3 illustrates an electrode assembly strut suitable for use in an electrode assembly.

Referring now to FIG. 3, there shown an electrode assembly strut 100 of the present disclosure. Electrode assembly strut 100 includes proximal end 102 and distal end 104. Proximal end 102 has proximal end minor width A and bushing tab 106 disposed thereon. Distal end 104 has distal end minor width B. Electrode assembly strut 100 further includes length C having a major width D, proximal taper zone length E, and distal taper zone length F. Minor width A, minor width B, and major width D are each measured along the surface of the electrode assembly strut from one edge to the opposing edge, as shown in FIG. 3. Contained within length C, is electrode tab 108 and electrode notches 110.

Length C is the portion of electrode assembly strut 100 that has a generally constant major width along its length, with the exception that the width becomes slightly larger for a short distance at electrode tab 108, as discussed below. Length C may be any suitable length for an electrode assembly strut and, in some embodiments, may be from about 0.200 inches (about 0.102 centimeters) to about 0.500 inches (about 1.27 centimeters), including from about 0.250 inches (about 0.635 centimeters) to about 0.450 inches (about 1.143 centimeters), including from about 0.250 inches (about 0.635 centimeters) to about 0.400 inches (about 1.016 centimeters), including about 0.300 inches (about 0.762 centimeters). In a specific embodiment, length C may be about 0.303 inches (0.769 centimeters). Along length C, electrode assembly strut 100 has major width D, which is the widest portion of electrode assembly strut 100. Major width D provides structural integrity to electrode assembly strut 100 and may be from about 0.018 inches (about 0.046 centimeters) wide to about 0.031 inches (about 0.079 centimeters) wide, including from about 0.020 inches (about 0.051 centimeters) wide to about 0.030 inches (about 0.076 centimeters) wide, including from about 0.025 inches (about 0.064 centimeters) wide to about 0.030 inches (about 0.076 centimeters) wide, including about 0.026 inches (about 0.066 centimeters) wide. Along with Length D, the thickness of electrode assembly strut 100 provides structural integrity to electrode assembly strut 100. The thickness of electrode assembly strut 100 is generally constant along its entire length, including through length C, proximal taper zone E and distal taper zone F (and including bushing tab 106. The thickness of electrode assembly strut 100 is from about 0.004 inches (about 0.010 centimeters) to about 0.007 inches (about 0.018 centimeters). In one specific embodiment, the thickness is about 0.004 inches (about 0.010 centimeters). In another specific embodiment, the thickness is about 0.005 inches (about 0.013 centimeters). In another specific embodiment, the thickness is about 0.006 inches (about 0.015 centimeters). In another specific embodiment, the thickness is about 0.007 inches (about 0.018 centimeters).

In some embodiments of the present disclosure, electrode assembly strut 100 will have a major width:thickness ratio of from about 2.571 to about 7.750, including from about 2.600 to about 7.500, including from about 2.700 to about 7.000, including from about 2.800 to about 6.800, including from about 3.000 to about 6.500, including from about 3.500 to about 6.500, including from about 3.700 to about 6.500. In a specific embodiment, the major width:thickness ratio is about 3.714. In another specific embodiment, the major width:thickness ratio is about 4.333. In another specific embodiment, the major width:thickness ratio is about 5.200. In another specific embodiment, the major width:thickness ratio is about 6.500.

Electrode assembly strut 100 has a proximal taper zone length E and a distal taper zone length F that are generally about equal in length, and in many embodiments, are equal in length. By providing the proximal and distal tapering as described herein on electrode assembly strut 100, electrode assembly strut 100 has significantly improved flexibility at both proximal end 102 and distal end 104 while maintaining rigidity along length C. Proximal taper zone length E and distal taper zone length F have a length of from about 0.080 inches (about 0.2032 centimeters) to about 0.150 inches (about 0.381 centimeters), including from about 0.100 inches (about 0.254 centimeters) to about 0.150 inches (about 0.381 centimeters), including from about 0.110 inches (about 0.279 centimeters) to about 0.145 inches (about 0.368 centimeters), including from about 0.120 inches (about 0.305 centimeters) to about 0.145 inches (0.368 centimeters). In many embodiments, proximal taper zone length E and distal taper zone length F are about 0.143 inches (about 0.363 centimeters) long.

Electrode assembly strut 100 further includes proximal end minor width A and distal end minor width B, which defines the width of electrode assembly strut 100 at proximal end 102 and distal end 104. Proximal end minor width A and distal end minor width B are generally about equal, and in many embodiments, are equal. Proximal end minor width A and distal end minor width B are from about 0.010 inches (about 0.025 centimeters) to about 0.015 inches (about 0.038 centimeters), including from about 0.011 inches (about 0.028 centimeters) to about 0.014 inches (about 0.036 centimeters), including from about 0.012 inches (about 0.030 centimeters) to about 0.014 inches (about 0.036 centimeters). In many embodiments, proximal end minor width A and distal end minor width B are about 0.012 inches (about 0.030 centimeters).

As noted above, electrode assembly strut 100 includes bushing tab 106 disposed on proximal end 102, electrode tab 108, and electrode notches 110. Bushing tab 106 is positioned on electrode assembly strut 100 such that when electrode assembly strut 100 is utilized in the manufacture of an electrode assembly, electrode assembly strut 100 can be properly positioned within an annular flange inside of a bushing, as is known in the art. Bushing tab 106 prevents the electrode assembly strut 100 from becoming improperly positioned as bushing tab 106 mates up directly against the bushing that houses the annular flange such that the bushing cannot move along electrode assembly strut 100. Electrode tab 108 and electrode notches 110 are both used to properly align and seat an electrode (not shown in FIG. 3) on electrode assembly strut 100. Because an electrode has a width that is greater than the width of the strut upon which it is seated, electrode tab 108 may be used to slightly increase the width of electrode assembly strut 100 such that an electrode may be aligned and oriented properly. In particular, in some embodiments, each electrode tab 108 may increase the width of electrode assembly strut 100 by up to 0.010 inches (0.0254 centimeters), including up to 0.009 inches (0.02286 centimeters), including up to 0.008 inches (0.02032 centimeters), including up to 0.007 inches (0.01778 centimeters), and including 0.006 inches (0.01524 centimeters). Similarly, electrode notches 110 are used to align the edge of the electrode with electrode notches 110 to assist in properly positioning the electrode onto electrode assembly strut 100. In particular, in some embodiments, each of electrode notches 110 may decrease the width of electrode assembly strut 100 by up to 0.003 inches (0.00762 centimeters), including up to 0.002 inches (0.00508 centimeters).

To further increase the strength of electrode assembly strut 100, and hence the resistance to radial compression of an electrode assembly incorporating electrode assembly strut 100 when in an expanded configuration, electrode assembly strut 100 includes a curved cross section, which adds to the overall stiffness of the strut over its entire length. The curved cross section has a radius of curvature of from about 0.015 inches (about 0.038 centimeters) to about 0.030 inches (about 0.076 centimeters), including from about 0.015 inches (about 0.038 centimeters) to about 0.025 inches (about 0.064 centimeters), including from about 0.015 inches (about 0.038 centimeters) to about 0.023 inches (about 0.058 centimeters), including from about 0.018 inches (about 0.046 centimeters) to about 0.023 inches (about 0.058 centimeters). In some embodiments, the radius of curvature of the curved cross section will be about 0.021 inches (0.053 centimeters).

Once the desired parameters of electrode assembly strut 100 are chosen as described above to provide an electrode assembly strut with superior flexibility and strength, electrode assembly strut 100 may be manufactured for use in an electrode assembly using conventional strut manufacturing methods that incorporate the novel design choices described herein. In many manufacturing methods, a unitary tube of a material having sufficient strength and shape memory characteristics, such as nitinol, is used. In many desirable embodiments, the nitinol will have an active austenitic finish temperature ($A_f$) of from −10° C. to 25° C., including from 0° C. to 25° C. The $A_f$ is a finished material property that is measured after heat treatment of the nitinol. This is the temperature at which the material has completely transformed to Austenite, which means that at and above this temperature the material will have completed its shape memory transformation or will display its superelastic characteristics. A suitable starting nitinol tube may have an outer diameter of about 0.0505 inches (about 0.1283 centimeters) and an inner diameter of about 0.0420 inches (about 0.1066 centimeters). However, the dimensions of the starting nitinol tube as well as the material or materials from which it is constructed may be other than as set forth above and remain with the scope of this disclosure. Once a suitable material, such as nitinol, is selected, the desired pattern of struts based on the selected design choices is cut into the material as is known in the art and the strut formed.

Once the electrode assembly strut is formed, it may optionally be subjected to a process to introduce a polymer layer, generally in the form of a polymer tube or polymer tubes, onto the surface to further tailor the rigidity, flexibility, and drag of the strut to a desired level, prior to incorporating it into an electrode assembly. A reflow process that utilizes a heat shrink material is suitable. The polymer layer may be formed of a single layer of material (such as from a single tube stretched over the length of the electrode assembly strut, or from two tubes with one introduced on the distal end of the electrode assembly strut and the other introduced on the proximal end of the electrode assembly strut), or it may be formed from two or more layers of material, with each of the two or more layers of material having a different durometer value. Coextruded polymer materials are desirable in many embodiments of the present disclosure. Suitable materials for forming the polymer coating include thermoplastic materials, with polyether block amides (Pebax® materials) and urethanes being particularly desirable. The polymer layer will generally have a thickness of from about 0.003 inches (about 0.008 centimeters) to about 0.005 inches (about 0.013 centimeters), including about 0.004 inches (about 0.010 centimeters). In many embodiments when a coating is to be introduced onto an electrode assembly strut, it will be in the form of a tube and an electrode as described herein may be slid over the tube and the tube/electrode combination slid over the strut prior to a reflow process such that any electrode wiring is contained between the strut and the polymer material. In one desirable embodiment, the electrode assembly strut includes a coextruded layer of material wherein an inner layer is constructed of a Pebax® material having a durometer value of about 93A and an outer layer is constructed of a urethane material having a durometer value of about 65D.

In one specific embodiment A of the present disclosure, electrode assembly strut 100 has length C of about 0.303 inches (about 0.769 centimeters), a length E of about 0.143 inches (about 0.363 centimeters), a length F of about 0.143 inches (about 0.363 centimeters), a width A of about 0.012 inches (about 0.030 centimeters), a width B of about 0.012 inches (about 0.030 centimeters), a width D of about 0.026 inches (about 0.066 centimeters), a thickness of about 0.005 inches (about 0.013 centimeters), and an $A_f$ of −10° C. to 25° C. In another specific embodiment B of the present disclosure, electrode assembly strut 100 has all of the same values of specific embodiment A, with the exception that it has a thickness of about 0.004 inches (about 0.010 centimeters). In another specific embodiment C of the present disclosure, electrode assembly strut 100 has all of the same values of specific embodiment A, with the exception that it has a thickness of about 0.006 inches (about 0.015 centimeters). In another specific embodiment D of the present disclosure, electrode assembly strut 100 has all of the same value of specific embodiment A, with the exception that it has a thickness of about 0.007 inches (about 0.018 centimeters).

Figure 4:
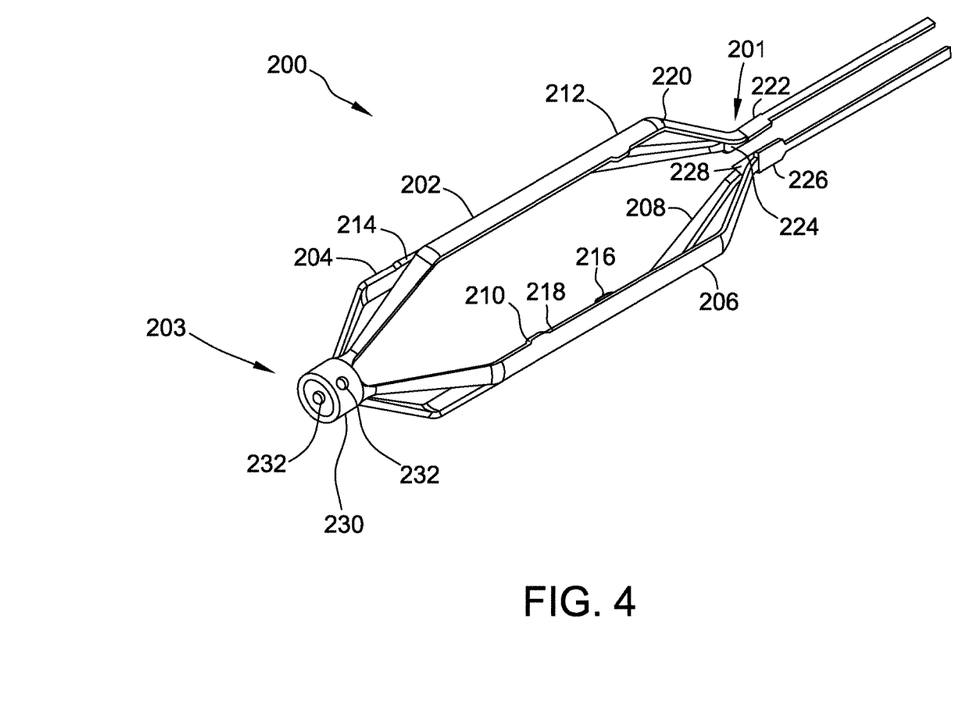
FIG. 4 illustrates an electrode assembly incorporating an electrode assembly strut as illustrated in FIG. 3.

Once the strut has been formed to the desired design parameters, it can be utilized to form an electrode assembly as described herein. Referring now to FIG. 4, there is shown an electrode assembly 200 having proximal end 201 and distal end 203 and including electrode assembly struts 202, 204, 206, and 208. Although illustrated in FIG. 4 as including four electrode assembly struts, electrode assemblies including more or less struts are within the scope of the disclosure, and FIG. 4 should be viewed as illustrative and not limiting; that is, electrode assemblies including 2, 3, 5, 6 or more electrode assembly struts are all within the scope of the present disclosure. All or only some of the electrode assembly struts may include one or more electrodes. Additionally, although each of the electrode assembly struts 202, 204, 206, and 208 are illustrated in FIG. 4 without a polymer coating, it is within the scope of the present disclosure for some or all of the electrode assembly struts to include a polymer coating as described herein. Electrode assembly strut 202 includes electrode tab 212 and electrode notches 220, electrode assembly strut 204 includes electrode tab 214, electrode assembly strut 206 includes electrode tab 210 and electrode notches 218, and electrode assembly strut 208 includes electrode tab 216. Electrode assembly struts 202, 204, 206, and 208 each also include bushing tab 222, 224, 226, and 228. Bushing tabs 222, 224, 226, and 228 will mate up against a bushing (not shown in FIG. 4) during processing to properly seat each electrode assembly strut, as noted above. Electrode assembly 200 additionally includes connecting ring 230 integrally positioned on distal end 203 for accepting each electrode assembly strut. Hole 232 is present on connecting ring for the introduction of an adhesive for bonding, as is known in the art.

The electrode assembly struts as disclosed and described herein are designed to carry at least one electrode thereon when incorporated into an electrode assembly, although it is within the scope of the present disclosure for the electrode assembly struts to be used without an electrode. An electrode is positioned generally on and around electrode tab 108 on length C of electrode assembly strut 100 as shown in FIG. 3, with notches 110 being utilized to align the edges of the electrodes. Because the electrodes are positioned on and around the electrode assembly strut, they protrude away from the strut and can impact the profile (i.e., the height) of a collapsed electrode assembly basket, and hence impact the size of an opening or channel that the electrode assembly can fit through without damage.

In accordance with one embodiment of the present disclosure, low profile, or kidney bean shaped electrodes suitable for use on an electrode assembly strut for incorporation into an electrode assembly are disclosed. The disclosed low profile electrodes provide for a reduced profile as they allow room for an activation or pull wire as described above to fit underneath the electrode, which allows the electrode to further collapse and reduce the overall profile of the electrode assembly. Additionally, the reduced profile of the electrode reduces the amount of drag such that it can more easily be passed through a guide catheter, such as a 6 French guide catheter, or other sized guide catheter or similar device.

Figure 5:
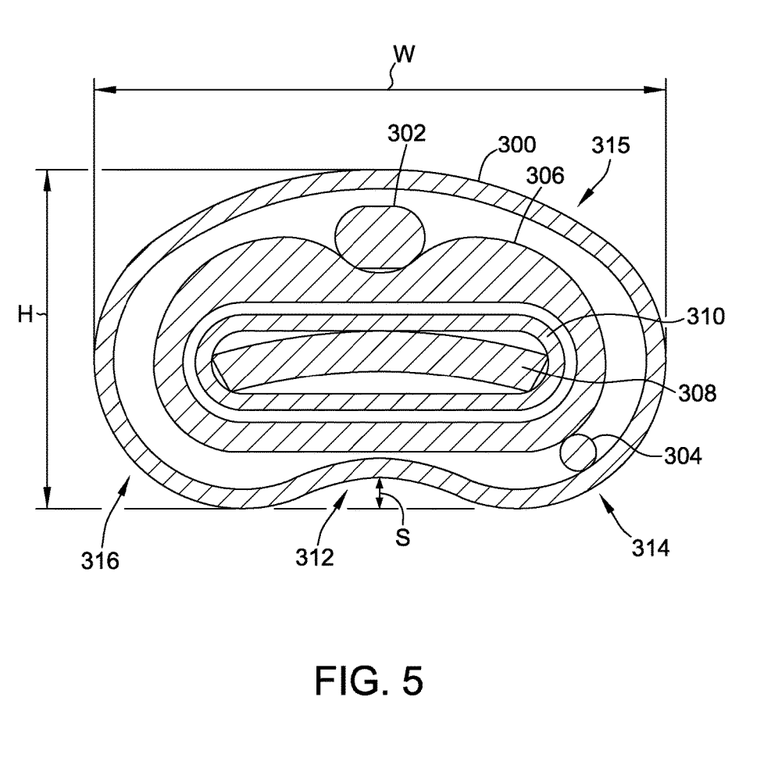
FIG. 5 is an axial cross-sectional view of a low profile electrode of the present disclosure mounted on an electrode assembly strut.

Referring now to FIG. 5, there is shown a low profile electrode 300 mounted on an electrode assembly strut 308. Low profile electrode 300 has a height H and a width W, and includes thermal sensor wire 302, electrode wire 304, and electrode support tubing 306. An adhesive (not shown) fills the space between low profile electrode 300 and electrode support tubing 306 to assist in holding thermal sensor wire 302 and electrode wire 304 in place and stabilizing low profile electrode 300. Electrode assembly strut 308, which is illustrated in FIG. 5 as having a curved cross section, is surrounded by polymer tubing 310. Low profile electrode 300 additionally includes a concave underside center indicated generally at 312, curved underside corners indicated generally at 314 and 316, and a curved top portion indicated generally at 315. Concave underside center 312 has a depth S.

Low profile electrode 300 has a width W and height H that provide a significantly reduced profile to facilitate passage through a guide catheter or similar device, and specifically a 6F guide catheter or other sized catheters. Width W is suitably no more than 0.067 inches (0.170 centimeters), or even no more than 0.065 inches (0.165 centimeters), or even no more than 0.063 inches (0.160 centimeters), or even no more than 0.061 inches (0.155 centimeters), or even no more than 0.060 inches (0.152 centimeters), or even no more than 0.059 inches (0.149 centimeters). In some specific embodiments, width W may be about 0.051 inches (about 0.129 centimeters), or even 0.052 inches (0.132 centimeters), or even 0.053 inches (0.135 centimeters), or even 0.054 inches (0.137 centimeters), or even 0.055 inches (0.139 centimeters), or even 0.056 inches (0.142 centimeters), or even 0.057 inches (0.145 centimeters), or even 0.058 inches (0.147 centimeters), or even 0.059 inches (0.149 centimeters). In another specific embodiment, width W may be 0.059 inches+/−0.008 inches (0.149 centimeters+/−0.020 centimeters). Height H is suitably no more than 0.031 inches (0.07874 centimeters), or even 0.030 inches (0.0762 centimeters), or even 0.029 inches (0.074 centimeters), or even no more than 0.028 inches (0.071 centimeters), or even no more than 0.027 inches (0.069 centimeters), or even no more than 0.026 inches (0.066 centimeters), or even no more than 0.025 inches (0.064 centimeters), or even no more than 0.024 inches (0.061 centimeters), or even no more than 0.023 inches (0.058 centimeters). In a specific embodiment, height H is about 0.029 inches (about 0.074 centimeters). In one specific embodiment of the present disclosure, low profile electrode 300 has a width W of about 0.059 inches+/−0.008 inches (about 0.149 centimeters+/−0.020 centimeters) and a height H of no more than 0.029 inches (0.074 centimeters).

As noted above, low profile electrode 300 also includes concave underside center 312 having depth S. Concave underside center 312 allows low profile electrode 300 to have a significantly reduced profile when the electrode assembly to which low profile electrode 300 is attached is in a collapsed configuration; that is, because the concave underside center 312 is in a concave position, the activation or pull wire that runs through the middle of the electrode assembly as discussed above in reference to FIGS. 1 and 2 and controls the configuration of the electrode assembly, can fit up snugly into the concave opening thus allowing low profile electrode 300 to reduce its profile by sitting lower. With multiple electrodes on an electrode assembly, the concave underside centers can significantly reduce the overall profile of the electrode assembly. Concave underside center 312 will generally have a depth S of from about 0.002 inches (about 0.0051 centimeters) to about 0.009 inches (about 0.023 centimeters), including from about 0.002 inches (about 0.005 centimeters) to about 0.007 inches (about 0.018 centimeters), including from about 0.002 inches (about 0.005 centimeters) to about 0.005 inches (0.013 centimeters). In specific embodiments, concave underside center 312 may have a depth of about 0.004 inches (about 0.010 centimeters), or even 0.005 inches (0.013 centimeters), or even 0.006 inches (0.015 centimeters), or even 0.007 inches (0.018 centimeters), or even 0.008 inches (0.020 centimeters), or even 0.009 inches (0.023 centimeters).

In addition to the specific depth that concave underside center 312 has on low profile electrode 300, it also has a specific radius of curvature to facilitate reducing the profile of low profile electrode 300. The radius of curvature of concave underside center 312 is from about 0.015 inches (about 0.038 centimeters) to about 0.025 inches (about 0.064 centimeters), including from about 0.017 inches (0.043 centimeters) to about 0.023 inches (about 0.058 centimeters), including from about 0.018 inches (about 0.046 centimeters) to about 0.021 inches (0.053 centimeters), including about 0.019 inches (about 0.048 centimeters).

To further reduce the profile and drag of low profile electrode 300, low profile electrode 300 includes curved underside corners 314 and 316, which reduce the amount of drag of low profile electrode when moving through a delivery catheter or similar device. Specifically, curved underside corners 314 and 316 will have a radius of curvature of from about 0.005 inches (about 0.0127 centimeters) to about 0.020 inches (about 0.051 centimeters), including from about 0.010 inches (about 0.025 centimeters) to about 0.020 inches (about 0.051 centimeters), including from about 0.012 inches (about 0.030 centimeters) to about 0.018 inches (about 0.046 centimeters), including from about 0.014 inches (about 0.036 centimeters) to about 0.016 inches (0.041 centimeters), including about 0.015 inches (about 0.038 centimeters). In addition, curved top portion 315 will have a radius of curvature of about 0.038 inches (about 0.09652 centimeters).

In one specific embodiment of the present disclosure, low profile electrode 300 has a height H of no more than 0.029 inches (0.074 centimeters), a width W of 0.059 inches+/−0.008 inches (0.149 centimeters+/−0.020 centimeters), a depth D of about 0.005 inches (about 0.013 centimeters), a concave underside center radius of curvature of about 0.019 inches (about 0.048 centimeters), and curved underside corners having a radius of curvature of about 0.015 inches (about 0.038 centimeters).

Low profile electrode 300 may be constructed of any material suitable and known in the art for constructing electrodes for use in ablation systems. Some exemplary suitable materials include metal or metal alloy materials. Examples of metal materials include platinum, titanium, tantalum, iridium, and niobium, and alloys thereof and combinations thereof. Some exemplary alloys include platinum/iridium alloys, nickel-cobalt-chromium-molybdenum alloys, iron-nickel-cobalt alloys, and the like.

To obtain the desired kidney bean shape of low profile electrode 300, a suitably sized rounded electrode is first formed with a fixture into an oval or "D" shape to assist in the loading of the electrode onto an electrode assembly strut. In one particular embodiment, the rounded electrode is formed into an oval shape having a height of about 0.032 inches (about 0.08128 centimeters). The now oval or "D" shaped electrode is then bonded to the thermocouple wire and loaded onto the electrode assembly strut. Once the electrode is loaded onto the electrode assembly strut, the final kidney bean shape including the desired dimensions as set forth above is formed by crimping the electrode using a fixture having the desired final shape of the electrode. Further, in some embodiments, an adhesive fillet, known to those skilled in the art, may be used to create a smooth transition at the edge of each electrode.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. An electrode assembly strut for an electrode assembly, the electrode assembly having the form of an electrode basket, the strut having a major width:thickness ratio of from about 2.571 to about 7.750, a minor width on a proximal end and a distal end of from about 0.010 inches to about 0.015 inches, a proximal taper zone extending in a distal direction from the proximal end having the minor width, a distal taper zone extending in a proximal direction from the distal end having the minor width, a major width located distal to the proximal taper zone and located proximal to the distal taper zone, the major width extending between a distal end of the proximal taper zone and a proximal end of the distal taper zone, wherein the minor width is less than the major width, and an austenitic finish temperature ($A_f$) of from −10° C. to 25° C., wherein the strut has a curved cross section.

2. The electrode assembly strut of claim 1 wherein the strut has a proximal taper zone length and a distal taper zone length of from about 0.080 inches to about 0.150 inches.

3. The electrode assembly strut of claim 2 wherein the proximal taper zone length and the distal taper zone length is about 0.143 inches.

4. The electrode assembly strut of claim 3 wherein the major width is from about 0.018 inches to about 0.031 inches.

5. The electrode assembly strut of claim 4 wherein the minor width is about 0.012 inches.

6. The electrode assembly strut of claim 1 wherein the curved cross section of the strut has a radius of curvature of from about 0.015 inches to about 0.030 inches.

7. The electrode assembly strut of claim 1 wherein the strut includes a polymer layer disposed thereon.

8. The electrode assembly strut of claim 7 wherein the polymer layer has a thickness of from about 0.003 inches to about 0.005 inches.

9. The electrode assembly strut of claim 1 wherein the strut includes an electrode alignment tab thereon.

* * * * *